(12) United States Patent
Nirmalakhandan et al.

(10) Patent No.: US 8,343,749 B2
(45) Date of Patent: Jan. 1, 2013

(54) METHOD AND APPARATUS FOR MEMBRANE-BASED, TWO-STAGE GAS PRODUCTION FROM SOLID BIOMATERIALS

(75) Inventors: Nagamany Nirmalakhandan, Las Cruces, NM (US); Shuguang Deng, Las Cruces, NM (US); Geoffrey Smith, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 0 days.

(21) Appl. No.: 13/347,012

(22) Filed: Jan. 10, 2012

(65) Prior Publication Data
US 2012/0107895 A1 May 3, 2012

Related U.S. Application Data

(62) Division of application No. 12/011,121, filed on Jan. 23, 2008, now Pat. No. 8,093,041.

(60) Provisional application No. 60/886,250, filed on Jan. 23, 2007.

(51) Int. Cl.
*C12N 1/00* (2006.01)
*C12P 1/00* (2006.01)
*C12M 1/00* (2006.01)

(52) U.S. Cl. .......... 435/243; 435/252.1; 435/252.4; 435/41; 435/292.1; 435/289.1; 435/287.1; 435/297.2; 435/299.1; 435/304.1

(58) Field of Classification Search .......... 435/243, 435/252.1, 252.4, 41, 292.1, 289.1, 297.1, 435/297.2, 299.1, 304.1
See application file for complete search history.

(56) References Cited

U.S. PATENT DOCUMENTS

| 5,464,539 | A | 11/1995 | Ueno et al. |
| 5,599,451 | A | 2/1997 | Guiot |
| 5,714,384 | A * | 2/1998 | Wilson et al. ............... 435/401 |
| 5,804,424 | A | 9/1998 | Kaplan et al. |
| 6,573,214 | B2 | 6/2003 | Abdo et al. |
| 6,673,742 | B2 | 1/2004 | Abdo et al. |
| 6,860,996 | B2 | 3/2005 | Noike et al. |
| 6,887,692 | B2 | 5/2005 | Paterek |
| 7,008,538 | B2 * | 3/2006 | Kasparian et al. .......... 210/610 |
| 7,067,453 | B1 | 6/2006 | Ming et al. |
| 7,083,956 | B2 * | 8/2006 | Paterek ...................... 435/168 |
| 7,138,046 | B2 | 11/2006 | Roychowdhury |

(Continued)

FOREIGN PATENT DOCUMENTS
JP 2001078754 3/2001
(Continued)

OTHER PUBLICATIONS

"Carbon Dioxide Membrane Principles and MEDAL Membrane", http://www.medal.airliquide.com/en/co-membrane/co-membrane-technology.html.

(Continued)

*Primary Examiner* — Nathan Bowers
(74) *Attorney, Agent, or Firm* — Deborah A. Peacock; Samantha A. Updegraff; Peacock Myers, P.C.

(57) ABSTRACT

Embodiments of the present invention preferably relate to a method and apparatus for a two-stage membrane-based production of gas, preferably hydrogen gas or the like, from solid biological materials, preferably organic waste materials or the like, comprising anaerobic hydrolysis and fermentation and photofermentation using microorganisms.

13 Claims, 19 Drawing Sheets

U.S. PATENT DOCUMENTS

| | | | |
|---|---|---|---|
| 7,144,566 | B2 | 12/2006 | Anzai et al. |
| 2002/0185437 | A1 | 12/2002 | Haridas et al. |
| 2003/0168403 | A1 | 9/2003 | Corcho-Sanchez et al. |
| 2004/0129135 | A1 | 7/2004 | Roark et al. |
| 2005/0064577 | A1* | 3/2005 | Berzin .................. 435/266 |
| 2006/0011757 | A1 | 1/2006 | Palm |
| 2006/0118485 | A1 | 6/2006 | Gallagher et al. |
| 2006/0272956 | A1 | 12/2006 | Felder et al. |
| 2006/0292685 | A1 | 12/2006 | Diz et al. |

FOREIGN PATENT DOCUMENTS

| | | |
|---|---|---|
| WO | WO-2006/061390 A1 | 6/2006 |

OTHER PUBLICATIONS

"Environmental monitoring by feedlots", United States Department of Agriculture, Animal and Plant Health Inspection Service, Veterinary Services, Jan. 1995.

"Guide Manual on NPDES Regulations for Concentrated Animal Feeding Operations", United States Environmental Protection Agency, Office of Water, EPA833-B-95-001, Dec. 1995.

"Multi-stage Membrane Systems for Pipeline and Offshore and benefits", http://www.medal.airliquide.com/en/co-membrane/co2-membrane-natural-gas-sweetening/natural-gas-sweetening-pipeline-and-offshore.html.

"Standard Methods for the examination of water and wastewater", American Public Health Association, Washington, D.C., 1998, 5-17.

Akkerman, Ida et al., "Photobiological hydrogen production: photochemical efficiency and bioreactor design", International Journal of Hydrogen Energy, vol. 27, Elsevier Science Ltd., 2002, 1195-1208.

Anderson, Ken et al., "Anaerobic treatment processes", The Handbook of Water and Wastewater Microbiology, Elsevier, 2003, 391-426.

Barlaz, Morton A. et al., "Methane Production from Municipal Refuse: A Review of Enhancement Techniques and Microbial Dynamics", Critical Reviews in Environmental Control, vol. 19, Issue 6, 1990, 557-584.

Batstone, D. J. et al., "The IWA Anaerobic Digestion Model No. 1.(ADM1)", Water Science and Technology, vol. 45, No. 1, IWA Publishing, 2002, 65-73.

Beneman, John R. , "The Technology of Biohydrogen", Biohydrogen, Ed. Zaborsky et al, Plenum Press, New York, 1998, 19-30.

Benemann, John R. , "Hydrogen production by microalgae", Journal of Applied Phycology, vol. 12, Kluwer Academic Publishers, Netherlands, 2000, 291-300.

Bernard, Olivier et al., "Dynamical Model Development and Parameter Identification for an Anaerobic Wastewater Treatment Process", Biotechnology and Bioengineering, vol. 75, No. 4, Nov. 20, 2001, 424-438.

Borzacconi, Liliana et al., "Hydrolysis Constant and VFA Inhibition in Acidogenic Phase of MSW Anaerobic Degradation", Wat. Sci. Tech., vol. 36, No. 6-7, Elsevier Science, Ltd., Great Britain, 1997, 479-484.

Bryers, J. D. , "Structured Modeling of the Anaerobic Digestion of Biomass Particulates", Biotechnology and Bioengineering, vol. XXVII, John Wiley & Sons, Inc., 1985, 638-649.

Chandler, J. A. et al., "Predicitng methane fermentation.biodegradability", Biotechnology and Bioengineering Symp. No. 10, Joihn Wiley & Sons, Inc., 1980, 93-107.

Chang, Feng-Yung et al., "Biohydrogen production using an up-flow anaerobic sludge blanket reactor", International Journal of Hydrogen Energy, vol. 29, Elsevier Ltd., 2004, 33-39.

Chang, Jo-Shu et al., "Biohydrogen production with fixed-bed bioreactors", International Journal of Hydrogen Energy, vol. 27, Elsevier Science Ltd., 2002, 1167-1174.

Contois, D. E. , "Kinetics of Bacterial Growth: Relationship between Population Density and Specific Growth Rate of Continuous Cultures", J. gen. Microbiol., vol. 21, 1959, 40-50.

Das, Debabrata et al., "Hydrogen production by biological processes: a survey of literature", International Journal of Hydrogen Energy, vol. 26, Elsevier Science Ltd., 2001, 13-28.

De Lorenzo, Victor et al., "Analysis and Construction of Stable Phenotypes in Gram-Negative Bacteria with Tn-5 and Tn10-Derived Minitransposons", Methods in Enzymology, vol. 235, Academic Press, Inc., 1994, 386-405.

Dehority, B. A. , "Degradation and Utilization of Isolated Hemicellulose by Pure Cultures of Cellulolytic Rume Bacteria", Journal of Bacteriology, vol. 80, No. 6, American Society for Microbiology, Jun. 1965, 1515-1520.

Dehority, B. A. et al., "Digestibility of Forage Hemicellulose and Pectin by Rumen Bacteria In Vitro and the Effect of Linification Thereon", J. Dairy Sci., vol. 45, 1962, 508-512.

Denac, M. et al., "Modeling Dynamic Experiments on the Anaerobic Degradation of Molasses Wastewater", Biotechnology and Bioengineering, vol. 31, John Wiley & Sons, Inc., 1988, 1-10.

Deng, S. G. et al., "Microwave heating synthesis of supported sorbents", Chemical Engineering Science, vol. 52, No. 10, Elsevier Science Ltd. Great Britain, 1997, 1563-1575.

Deng, S. G. et al., "Microwave synthesis of mesoporous and microporous alumina powders", Journal of Materials Science Letters, vol. 16, Chapman & Hall, 1997, 1291-1294.

Deng, S. G. et al., "Sol-Gel Preparation and Properties of Alumina Adsorbents for Gas Separation", AIChE Journal, vol. 41, No. 3, Mar. 1995, 559-570.

Deng, S.G. et al., "Granulation of Sol-Gel-Derived Nanostructured Alumina", AIChE Journal, vol. 43, No. 2, Feb. 1997, 505-514.

Eastman, John A. et al., "Solubilization of particulate organic carbon during the acid phase of anaerobic digestion", Jounral WPCF, vol. 53, No. 3, 1981, 352-366.

El-Mashad, H. M. et al., "A dispersion based model for anaerobic digestion of solid cattle wastes in a stratified thermophilic accumulation system", Water Science & Technology, vol. 52, No. 1-2, IWA Publishing, 2005, 193-202.

Eroglu, E. et al., "The Relationship Between Groth Kinetics and Hydrogen Production by Rodobacter Spaeroides", EPMR-2000, Cyprus, 2000.

Fan, Yaoting et al., "Optimization of initial substrate and pH levels for germination of sporing hydrogent-producing anaerobes in cow dung compost", Bioresource Technology, vol. 91, 2004, 189-193.

Fernandez, F.G. A. et al., "Modeling of Biomass Productivity in Tubular Photobioreactors for Microalgal Cultures: Effects of Dilution Rate, Tube Diameter, and Solar Irradiance", Biotechnology and Bioengineering, vol. 58, No. 6, John Wiley & Sons, Inc., Jun. 20, 1998, 605-616.

Frigon, D. et al., "Who eats what? Classifying microbial populations based on diurnal profies of rRNA levels", Water Science and Technology, vol. 46, No. 1-2, IWA Publishing, 2002, 1-9.

Gavalas, G. R. et al., "Deposition of H2-Permselective SiO2 Films", Chemical Engineering Science, vol. 44, No. 9, Pergamon Press, Great Britain, 1989, 1829-1835.

Ghaly, A. E. et al., "Kinetics of an Intermittent-Flow, Continuous-Mix Anaerobie Reactor", Energy Sources, vol. 22, Taylor & Francis, 2000, 525-542.

Ghosh, S. et al., "Bioconversion of Water Hyacinth-Coastal Bermuda Grass-MSW-Sludge Blends to Methane", Biotechnology and Bioengineering Symposium, No. 10, John Wiley & Sons, Inc., 1980, 163-187.

Ghosh, S. , "Gasification of Concentrated Particulate and Solid Substrates by Biphasic Anaerobic Digestion", Biotechnological Advances in Processing Municiapt Waste for Fuels and Chemicals, ed. A.A. Antonopoulos, Noyes Data Corporation, Park Ridge, New Jersey, 1987, 303-320.

Gossett, James M. et al., "Anaerobic Digestion of Waste Activated Sludge", ASCE Jour. Env. Egrg., Presented at the Jul. 8-10, 1980, National Conference on Environmental Engineering, ASCE, New York, N.Y., Jul. 8, 1980, 1101-1120.

Gray, F. V. et al., "Origins of the Volatile Fatty Acids in the Rumen", Nature, No. 4322, Aug. 30, 1952, 375-376.

Gray, F. V. et al., "The Fermentation of Hemicellulose by Washed Suspensions of Rumen Bacteria", Aust. J. Agr. Res., vol. 9, 1958, 797-801.

Grobbelaar, Johan U. et al., "Use of photoacclimation in the design of a novel photobioreactor to achieve high yields in algal mass cultivation", Jounral of Applied Phycology, vol. 15, Kluwer Academic Publishers, The Netherlands, 2003, 121-126.

Gujer, W. et al., "Conversion Processes in Anaerobic Digestion", Wat. Sci. Tech., vol. 15, IAWPRC/Pergamon Press Ltd., Great Britain, 1983, 127-167.

Guwy, A. J. et al., "Hydrogen Production in a High Rate Fluidised Bed Anaerobic Digester", Wat. Res., vol. 31, No. 6, Elsevier Science Ltd., Great Britain, 1997, 1291-1298.

Hai-Lou, Xu et al., "A hybrid anaerobic solid-liquid bioreactor for food waste digestion", Biotechnology Letters, vol. 24, Aluwer Academic Publishers, Netherlands, 2002, 757-761.

Hashimoto, A. G. et al., "Anaerobic fermentation of beef catrtle manure", Final Report SERI/TR-98372-1, U.S. Department of Agriculture, Nebraska, Jan. 1981.

Hawkes, F. R. et al., "Sustainable fermentative hydrogen production: challenges for process optimisation", International Journal of Hydrogen Energy, vol. 27, Elsevier Science Ltd., 2002, 1339-1347.

Heukelekian, H. et al., "Transformation of Some Lipids in Anaerobic Sludge Digestion", Sewage and Industrial Wastes, vol. 30, No. 9, Sep. 1958, 1108-1120.

Higuchi, Y. et al., "Hydrolytic activity of alpha-amylase in anaerobic digested sludge", Water Science & Technology, vol. 52, No. 1-2, IWA Publishing, 2005, 259-266.

Hill, D. T. et al., "A dynamic model for simulation of animal waste digestion", Journal WPCF, Oct. 1977, 2129-2143.

Howard, B. H., "Hydrolysis of the Soluble Pentosans of Wheat Flour and Rhodymenia palmata by Ruminal Micro-organisms", Biochem. J., vol. 67, 1957, 643-651.

Huang, Andrew A., "Enzymatic Hydrolysis of Cellulose to Sugar", Biotechnol. & Bioeng. Symp., No. 5, John Wiley & Sons, Inc., 1975, 245-252.

Hussy, I. et al., "Continuous Fermentative Hydrogen Production from a Wheat Starch Co-Product by Mixed Microflora", Biotechnology and Bioengineering, vol. 84, No. 6, Wiley Periodicals, Inc., Dec. 20, 2003, 619-626.

Jordal, K. et al., "Integration of H2-separating membrane technology in gas turbine processes for CO2 capture", Energy, vol. 29, Elsevier Ltd., 2004, 1269-1278.

Kalyuzhnyi, S. V., "Batch Anaerobic Digestion of Glucose and Its Mathematical Modeling. II. Description, Verification and Application of Model", Bioresource Technology, vol. 59, Elsevier Science Limited Great Britain, 1997, 249-258.

Kayhanian, Masoud et al., "Development of a Mathematical Model for the Simulation of the Biodegradation of Organic Substrates in a High-Solids Anaerobic Digestion Process", J. Chem. Tech. Biotechnol., vol. 66, SCI, Great Britain, 1996, 312-322.

Kobayashi, Michiharu et al., "The Mass Culture and Cell Utilization of Photosynthetic Bacteria", Process Biochemistry, Sep. 1978, 27-30.

Koku, Harun et al., "Aspects of metabolism of hydrogen production by Rhodobacter sphaeroides", International Journal of Hydrogen Energy, vol. 27, Elsevier Science Ltd., 2002, 1315-1329.

Lay, Jiunn-Jyi, "Biohydrogen Generation by Mesophilic Anaerobic Fermentation of Microcrystalline Cellulose", Biotechnology and Bioengineering, vol. 74, No. 4, John Wiley & Sons, Inc., Aug. 20, 2001, 280-287.

Lay, Jiunn-Jyi et al., "Feasilibty of Biological Hydrogen Production from Organic Fraction of Municiapl Solid Waste", Wat. Res., vol. 33, No. 11, Elsevier Science Ltd., Great Britain, 1999, 2579-2586.

Lay, Jiunn-Jyi et al., "Influence of chemical nature of organic wastes on their conversion to hydrogen by heat-shock digested sludge", International Journal of Hydrogen Energy, vol. 28, Elsevier Ltd., 2003, 1361-1367.

Lay, Jiunn-Jyi, "Modeling and Optimization of Anaerobic Digested Sludge Converting Starch to Hydrogen", Biotechnology and Bioengineering, vol. 68, No. 3, John Wiley & Sons, Inc., May 5, 2000, 269-278.

Lee, Kuo-Shing et al., "Anaerobic Hydrogen Production with an Efficient Carrier-induced Granular Sludge Bed Bioreactor", Biotechnology and Bioengineering, vol. 87, No. 5, Wiley Periodicals, Inc., Sep. 5, 2004, 648-657.

Lee, Kuo-Shing et al., "H2 production with anaerobic sludge using activated-carbon supported packed-bed bioreactors", Biotechnology Letters, vol. 25, Kluwer Academic Publishers, The Netherlands, 2003, 133-138.

Lee, Yuan-Kun, "Microalgal mass culture systems and methods: Their limitation and potential", Journal of Applied Phycology, vol. 13, Kluwer Academic Publishers, The Netherlands, 2001, 307-315.

Lettinga, G., "Digestion and degradation, air for life", Water Science and Technology, vol. 44, No. 8, IWA Publishing, 2001, 157-176.

Levin, David B. et al., "Biohydrogen production: prospects and limitations to practial application", International Journal of Hydrogen Energy, vol. 29, Elsevier Ltd., 2004, 173-185.

Lin, C. Y. et al., "Anaerobic Hydrogen Production from Sucrose Using an Acid-Enriched Sewage Sludge Microflora", Eng. Life Sci., vol. 4, No. 1, Wiley-VCH Verlag GmbH & Co., Weinheim, 2004, 66-70.

Lin, Y. S. et al., "Sol-gel preparation of nanostructured adsorbents", Adsorption and Its Application in Industry and Environmental Protection, Studies in Surface Science and Catalysis, vol. 120, Ed. A. Dabrowski, Elsevier Science B.V., 1998, 653-686.

Logan, Bruce E. et al., "Biological Hydrogen Production Measured in Batch Anaerobic Respirometers", Environ. Sci. Technol., vol. 36, No. 11, American Chemical Society, 2002, 2530-2535.

Ma, Yi H. et al., "Thin Composite Palladium and Palladium/Alloy Membrances for Hydrogen Separation", Ann. N.Y. Acad. Sci., vol. 984, New York Academy of Sciences, 2003, 346-360.

Mahmoud, Nidal et al., "Anaerobic stabilisation and conversion of biopolymers in primary sludge-effect of temperature and slude retention time", Water Research, vol. 38, Elsevier, Ltd., 2004, 983-991.

Masse, D. I. et al., "Comprehensive Model of Anaerobic Digestion of Swine Manure Slurry in a Sequencing Batch Reactor", Wat. Res., vol. 34, No. 12, Elsevier Science Ltd., Great Britain, 2000, 3087-3106.

Mata-Alvarez, Joan, "a Dynamic Simulation of a Two-Phase Anaerobic Digestion System for Solid Wastes", Biotechnology and Bioengineering, vol. 30, John Wiley & Sons, Inc., 1987, 844-851.

Mata-Alvarez, Joan, "A Simulation Study of a Continuous Two-Phase Dry Digestion System", Biotechnology and Bioengineering, vol. 34, John Wiley & Sons, Inc., 1989, 609-616.

Miron, Asterio S. et al., "Bubble-Column and Airlift Photobioreactors for Algal Culture", AIChE Journal, vol. 46, No. 9, Sep. 2000, 1872-1887.

Miron, Yehuda et al., "The Role of Sludge Retention Time in the Hydrolysis and Acidification of Lipids, Carbohydrates and Proteins During Digestion of Primary Sludge in CSTR Systems", Wat. Res., vol. 34, No. 5, Elsevier Science Ltd., Great Britain, 2000, 1705-1713.

Miyake, Jun, "The Science of Biohydrogen", Biohydrogen, Ed. Zaborsky, et al., Plenum Press, New York, 1998, 7-18.

Modigell, M. et al., "Reactor Development for a Biosolar Hydrogen Production Process", Renewable Energy, vol. 14, Nos. 1-4, Elsevier Science Ltd., Great Britain, 1998, 421-426.

Morales-Morales, Hugo A. et al., "Optimization of a Reusable Hollow-Fiber Ultrafilter for Simultaneous Concentration of Enteric Bacteria, Protozoa, and Viruses from Water", Applied and Environmental Microbiology, vol. 69, No. 7, American Society for Microbiology, Jul. 2003, 4098-4102.

Mosqueda, Gilberto et al., "A Set of Genes Encoding a Second Toluene Efflux System in *Pseudomonas putida* DOT-TIE is Linked to the tod Genes for Toluene Metabolism", Journal of Bacteriology, vol. 182, No. 4, American Society for Microbiology, Feb. 2000, 937-943.

Munch, Elisabeth V. et al., "Mathematical Modelling of Preferment-ers—I. Model Development and Verification", Wat. Res., vol. 33, No. 12, Elsevier Science Ltd., Great Britain, 1999, 2757-2768.

Myint, M. et al., "Anaerobic fermentation of cattle manure: Modeling of hydrolysis and acidogenesis", Water Research, vol. 41, Elsevier Ltd., 2007, 323-332.

Myint, M. et al., "Evaluation of First-Order, Second-Order, and Surface-Limiting Reactions in Anaerobic Hydrolysis of Cattle Manure", Environmental Engineering Science, vol. 23, No. 6, Mary Ann Liebert, Inc., 2006, 970-980.

Negri, E. D. et al., "A Mathematical Model of Volatile Fatty Acids (VFA) Production in Plug-Flow Reactor Treating the Organic Fracion of Municipal Solid Waste (MSW)", Wat. Sci. Tech., vol. 27, No. 2, IAWQ, Great Britain, 1993, 201-208.

Noykova, Nelly et al., "Quantitative Analyses of Anaerobic Wastewater Treatment Processes: Identifiability and Parameter Estimation", Biotechnology and Bioengineering, Vo. 78, No. 1, Wiley Periodicals, Inc., Apr. 5, 2002, 89-103.

Oh, Sang-Eun et al., "Biological Hydrogen Production Using a Membrance Bioreactor", Biotechnology and Bioengineering, vol. 8, No. 1, Wiley Periodicals, Inc., Jul. 5, 2004, 119-127.

Oh, Sang-Eun et al., "The Relative Effectiveness of pH Control and Heat Treatment for Enhancing Biohydrogen Gas Production", Environ. Sci. Technol., vol. 37, No. 22, American Chemical Society, Oct. 16, 2003, 5186-5190.

Oh, Sang-Eun et al., "The Relative Effectiveness of pH Control and Heat Treatment for Enhancing Biohydrogen Gas Production", Environmental Science & Technology, vol. 37, No. 22, American Chemical Society, 2003, 5186-5190.

Olivas, Yolanda et al., "The Influence of Redox Potential on the Degradation of Halogenated Methanes", Environmental Toxicology and Chemistry, vol. 21, No. 3, SETAC, USA, 2002, 493-499.

Omstead, D. R. et al., "Membrane-Controlled Digestion: Anaerobic Production of Methane and Organic Acids", Biotechnology and Bioengineering Symp., No. 10, John Wiley & Sons, Inc., 1980, 247-258.

Ong, H. K. et al., "Physical, Chemical and Biomethanation Characteristics of Stratified Cattle-Manure Slurry", Asian-Aus. J. Animal Sci., vol. 13, 2000, 1593-1597.

Orhon, Derin et al., "Experimental Basis for the Hydrolysis of Slowly Biodegradable Substrate in Different Wastewaters", Wat. Sci. Tech., vol. 39, No. 1, Elsevier Science Ltd., Great Britain, 1999, 87-95.

Palazzi, E. et al., "Process development of continuous hydrogen production by Enterobacter aerogenes in a packed column reactor", Bioprocess Engineering, vol. 22, Springer-Verlag, 2000, 205-213.

Palmisano,, Anna C. et al., "Introduction to Solid Waste Decomposition", Microbiology of Solid Waste, eds. A.C. Palmisano and M.A. Barlaz, CRC Press, New York, 1996, 1-30.

Pavlostathis, S. G. et al., "Kinetics of Anaerobic Treatment: A Critical Review", Critical Reviews in Environmental Control, vol. 21, Nos. 5-6, CRC Press, Inc., 1991, 411-490.

Pavlostathis, Spyros G. et al., "Prelminary Conversion Mechanisms in Anaerobic Digestion of Biological Sludges", ASCE J. Environ. Eng., vol. 114, No. 3, ASCE, Jun. 1988, 575-592.

Pingali, Kalyana C. et al., "Direct Synthesis of Ru-Ni Nanoparticles with Core-and-Shell Structure", Chem. Eng. Comm., vol. 194, Taylor & Francis Group, LLC., 2007, 780-786.

Pingali, Kalyana C. et al., "Silver Nanoparticles from Ultrasonic Spray Pyrolysis of Aqueous Silver Nitrate", Aerosol Science and Technology, vol. 39, American Association for Aerosol Research, 2005, 1010-1014.

Poulsen, O. M. et al., "A Standard Formula for the Determination of the Initial Rate of Hydrolysis of Carboxymethylcellulose", Biotechnology and Bioengineering, vol. 27, John Wiley & Sons, Inc., 1985, 409-414.

Ray, Bill T. et al., "Sludge Digestion by Anaerobic Fluidized Beds. II: Kinetic Model", Journal of Environmental Engineering, vol. 115, No. 6, ASCE, 1989, 1156-1170.

Robbins, John E. et al., "Methane Production from Cattle Waste and Delignified Straw", Infection and Immunity, vol. 38, No. 1, Jul. 1979, 175-177.

Rousset, Marc et al., "Hterologous Expression of the Desulfovibriogigas [NiFe] Hydrogenase in Desulfovibrio fructosovorans MR400", Journal of Bacteriology, vol. 180, No. 18, American Society for Microbiology, Sep. 1998, 4982-4986.

Ruel, S. M. et al., "Modeling Acidogenic and Sulfate-Reducing Processes for the Determination of Fermentable Fractions in Wastewater", Biotechnology and Bioengineering, vol. 80, No. 5, Wiley Periodicals, Inc., Dec. 5, 2002, 525-536.

Ruiz, Thomas R. et al., "Identification and characterization of nuclease activities in anaerobic environmental samples", Can. J. Microbiol., vol.46, NRC Canada, 2000, 736-740.

Sandhu, K. S. et al., "Prevalance of the eaeA gene in verotoxigenci Escherichia coli strains from dairy cattle in Southwest Ontario", Epidemiol. Infect., vol. 116, Cambridge University Press, 1996, 1-7.

Santana, L. et al., "Microbial Characterization, Enumeraion and Degradation Rates of Municipal Solid Waste Components in a Two-Phase Bioreactor", Poster #Q-328, Abstracts, American Society for Microbiology's 102nd General Meeting, Salt Lake City, Utah, May 19-23, 2002, 435.

Sasikala, K. et al., "Anoxygenic Phototrophic Bacteria: Physiology and Advances in Hydrogen Production Technology", Advances in Applied Microbiology, vol. 38, Academic Press, Inc., 1993, 211-295.

Shimamoto, Seiko et al., "Partial Characterization of an Enzyme Fraction with Protease Activity Which Converts the Spore Peptidoglycan Hydrolase (SleC) Prevursor to an Active Enzyme during Germination of Clostribidum perfringens S40 Spores and Analysis of a Gene Cluster . . .", Journal of Bacteriology, vol. 183, No. 12, American Society for Microbiology, Jun. 2001, 3742-3751.

Siegrist, H. et al., "Mathematical Moddling of Anaerobic Mesophilic Sewage Sludge Treatment", Wat. Sci. Tech., vol. 27, No. 2, IAWQ, Great Britain, 1993, 25-36.

Simeonov, IV. et al., "Dynamic Modeling of Mesophilic Anaerobic Digestion of Animal Waste", Wat. Res., vol. 30, No. 5, Elsevier Science Ltd. Great Britain, 1996, 1087-1094.

Sleat, R. et al., "Activities and Distribution of Key Microbial Groups in Landfill", Sanitary Landfilling: Process, Technology and Environmental Impact, Eds. Christenson, T.H. et al., Academic Press, Orlando, FL., 1989, 51-59.

Sung, Shihwu et al., "Performance of temperature-phased anaerobic digestion (TPAD) system treating dairy cattle wastes", Water Research, vol. 37, Elsivier Science Ltd., 2003, 1628-1636.

Tanisho, S. et al., "Fermentative Hydrogen Evolution by Enterobacter Aerogenes Strain E. 82005", Int. J. Hydrogen Energy, vol. 12, No. 9, 1987, 623-627.

Tellez, G. , "Biological treatment process for removing petroleum hudrocarbons from oilfield produced waters", Ph.D. Dissertation, New Mexico State Unversity, 1994.

Tsygankov, A. A. , "Laboratory Scale Photobioreactors", Applied Biochemistry and Microbiology, vol. 37, No. 4, 2001, 333-341.

Turner, John A. et al., "Hydrogen Economy based on Renewable Energy Sources", The Electrochemical Society Interface, Fall 2004, 24-30.

Uhlhom, R.J.R. , "Ceramic Membrances for Gas Separation: Synthesis and Transport Properties (abstract)", Ph.D. Thesis, University of Twente, The Netherlands, 1990.

Van Ginkiel, Steven et al., "Biohydrogen Production as a Function of pH and Substrate Concentration", Environ. Sci. Technol., vol. 35, American Chemical Society, Nov. 2, 2001, 4726-4730.

Van Groenestijn, J. W. et al., "Energy aspects of biological hydrogen production in high rate bioreactors operated in the thermophilic temperature range", International Journal of Hydrogen Energy, vol. 27, Elsevier Science Ltd., 2002, 1141-1147.

Van Horn, H. H. et al., "Components of Dairy Manure Management Systems", Journal of Dairy Science, vol. 77, No. 7, 1994, 2008-2030.

Van Niel, Ed W. et al., "Substrate and Product Inhibition of Hydrogen Production by the Extreme Thermophile, *Caldicellulosiruptor saccharolyticus*", Biotechnology and Bioengineering, vol. 81, No. 3, Wiley Periodicals, Inc., Feb. 5, 2003, 255-262.

Vavilin, V. A. et al., "A Description of Hydrolysis Kinetics in Anaerobic Degradation of Particulate Organic Matter", Bioresource Technology, vol. 56, Elsevier Science Limited Great Britain, 1996, 229-237.

Vavilin, Vastly A. et al., "Distributed Model of Solid Waste Anaerobic Digestion", Biotechnology and Bioengineering, vol. 81, No. 1, Wiley Periodicals, Inc., Jan. 5, 2003, 66-73.

Veeken, Adrie et al., "Effect of pH and VFA on Hydrolysis of Organic Solid Waste", Journal of Environmental Engineering, Dec. 2000, 1076-1081.

Veeken, Adrie et al., "Effect of temperature on hydrolysis rates of selected biowaste components", Bioresource Technology, vol. 69, 1999, 249-254.

White, James K. et al., "A framework to contain a spatially distributed model of the degradation of solid waste in landfills", Waste Manage Res, vol. 21, ISWA, U.K., 2003, 330-345.

Woods, Calvin E. et al., "Stage Digestion of Wastewater Sludge", Journal WPCF, vol. 37, No. 11, Nov. 1965, 1495-1505.

Yokoi, Haruhiko et al., "H2 production from starch by a mixed culture of *Clostridium butyricum* and *Rhodobacter* sp. M-19", Biotechnology Letters, vol. 20, No. 9, Chapman & Hall, Sep. 1998, 895-899.

Yu, H. W. et al., "Energy recovery from grass using two-phase anaerobic digestion", Waste Management, vol. 22, Elsevier Science Ltd., 2002, 1-5.

Yu, H.-Q. et al., "High-rate anaerobic hydrolysis and acidogenesis of sewage sludge in a modified upflow reactor", Water Science and Technology, Vo. 48, No. 4. IWA Publishing, 2003, 69-75.

Yu, Z. et al., "Dechlorination of polychlorinated methans by a sequential methanogenic-denitrifying bioreactor system", Appl Microbiol Biotechnol, vol. 53, Springer-Verlag, 2000, 484-489.

Zhang, Tong et al., "Biohydrogen production from starch in wastewater under thermophilic condition", Journal of Environmental Management, vol. 69, Elsevier Ltd., 2003, 149-156.

Zhu, Heguang et al., "Hydrogen production as a novel process of wastewater treatment—studies on tofu wastewater with entrapped *R. sphaeroides* and mutagenesis", International Journal of Hydrogen Energy, vol. 27, Elsevier Science Ltd., 2002, 1349-1357.

\* cited by examiner

METHOD AND APPARATUS FOR MEMBRANE-BASED, TWO-STAGE GAS PRODUCTION FROM SOLID BIOMATERIALS

CROSS-REFERENCE TO RELATED APPLICATIONS

This application is a divisional of U.S. patent application Ser. No. 12/011,121 (U.S. Pat. No. 8,093,041), entitled "Method and Apparatus for Membrane-Based, Two-Stage Gas Production from Solid Biomaterials", filed on Jan. 23, 2008 which claims priority to U.S. Provisional Patent Application Ser. No. 60/886,250, entitled "Membrane-Based Biohydrogenesis for Enhanced Biological Production of Hydrogen From Organic Wastes," filed on Jan. 23, 2007, and the specifications and claims of both applications are incorporated herein by reference.

STATEMENT REGARDING FEDERALLY-SPONSORED RESEARCH OR DEVELOPMENT

The U.S. Government has a paid-up license in this invention and the right in limited circumstances to require the patent owner to license others on reasonable terms as provided for by the terms of contract No. BES-06070175 awarded by the National Science Foundation and of Contract No. 601660 SU-83248501-0 awarded by the U.S. Environmental Protection Agency.

COPYRIGHTED MATERIAL

A portion of the disclosure of this patent document contains material that is subject to copyright protection. The owner has no objection to the facsimile reproduction by anyone of the patent document or patent disclosure, as it appears in the Patent and Trademark Office patent file or records, but otherwise reserves all copyrights whatsoever.

BACKGROUND OF THE INVENTION

1. Field of the Invention (Technical Field)

The present invention relates to a two-stage membrane-based apparatus and method for production of gas from biological materials using fermentative and photosynthetic processes.

2. Description of Related Art

Note that the following discussion refers to a number of publications by author(s) and year of publication, and that due to recent publication dates certain publications are not to be considered as prior art vis-à-vis the present invention. Discussion of such publications herein is given for more complete background and is not to be construed as an admission that such publications are prior art for patentability determination purposes.

Hydrogen ($H_2$) has been identified as a renewable and pollution-free high-efficiency carrier that has the potential to replace the nonrenewable fossil fuels of today. However, currently available $H_2$ production technologies, such as electrolysis or biomass gasification, are energy-intensive and expensive. Many technical challenges relating to hydrogen's generation, storage, and usage remain to be solved before it can be widely adapted for use.

Hydrogen can be produced by thermochemical, electrochemical, or biological processes. Of the three, biological processes are emerging as more environment-friendly, less energy-intensive, and sustainable. Recent research suggests that hydrogen produced via biological processes or from biomass, i.e. biohydrogen, is feasible, where the biomass is organic matter such as chemical feedstock or waste streams, and can be sustainable and cost-effective in the latter case. Current research has identified three processes as viable for biohydrogen production: biophotolysis by cyanobateria; photofermentation by anoxygenic phototrophic bacteria; and fermentation by anaerobic bacteria. The following are examples of such hydrogen production technologies.

U.S. Pat. No. 7,083,956 to Paterek, entitled "Method For Hydrogen Production From Organic Wastes Using a Two-Phase Bioreactor System", issued Aug. 1, 2006, discloses a method for hydrogen production from organic wastes and manures using a two-phase bioreactor system with biodegradable solid being introduced into first stage anaerobic bioreactor utilizing indigenous microflora. The liquid effluent, including fatty acids, is transferred into second stage anaerobic bioreactor, which is not photofermentative. Hydrogen passes through semi-permeable fibers of the second stage.

U.S. Pat. No. 6,887,692 to Paterek, entitled "Method and Apparatus For Hydrogen Production From Organic Wastes and Manure," issued May, 2005, discloses a method and system for hydrogen production in which a feedstock of at least one biodegradable solid is introduced into a first stage anaerobic bioreactor and a liquid effluent formed. A hollow fiber membrane separates liquid phases. The liquid effluent is transferred into a second stage anaerobic bioreactor having a plurality of hollow semipermeable fibers having an outer surface coated with a biofilm formed by at least one hydrogenogenic bacteria, which forms hydrogen gas within the lumen of the hollow semipermeable fibers. The hydrogen thus produced is removed from the lumen of the hollow semipermeable fibers.

U.S. Pat. No. 7,138,046 to Roychowdhury, entitled "Process For Production Of Hydrogen From Anaerobically Decomposed Organic Materials," issued Nov. 21, 2006, discloses a process for the production of hydrogen from anaerobically decomposed organic materials by applying an electric potential to anaerobically decomposed organic materials to form hydrogen gas.

Anaerobic technology has been proven to be energy-efficient in stabilizing organic waste streams. Reports from several laboratory studies and full-scale projects have documented successful applications of this technology in stabilizing liquid waste streams and generating energy in the form of gaseous methane. However, large-scale application of this technology in stabilizing particulate wastes to produce energy has been hindered by the poor kinetics of the overall process. Conversion of particulate organic wastes to gaseous methane involves multiple steps in series and parallel, diverse groups of microorganisms, and different environments.

The following have been recognized as important stages in the process. In the first stage, acidogenic organisms solubilize particulate substrates extracellularly by enzymatic hydrolysis. In the second stage, acidogenic organisms catabolize the products of the first stage into volatile organic acids, carbon dioxide, and hydrogen. In the next stage, acetogenic organisms convert the products of the second stage to acetic acid. Finally, methanogenic organisms convert the acetic acid to carbon dioxide and methane.

Hydrogen is removed by absorption in materials such as Pd and $LaNi_5$; stripping by boiling or by a recirculating gas such as nitrogen; or evaporation at large surface areas. However, these approaches are expensive, energy-intensive, or impractical for large-scale applications.

Typical gas components in biogas include $CH_4$, $N_2$, $CO_2$, $H_2O$ (vapor) and trace amounts of $NH_3$, $H_2S$, and $HCl$. Traditional biogas separation processes focus on $CH_4$ enrichment, which is similar to $CO_2$ separation from natural gas. Both adsorption and membrane processes have previously been applied in biogas separation. A hollow fiber membrane separation process for natural gas upgrade has been commercialized by Air Liquide (MEDAL-Air Liquid). Palladium and alloy membranes for $H_2$ separation from gas mixtures have been extensively studied and documented. The mechanism of $H_2$ transport through such membranes involves the following series of steps: adsorption; dissociation; ionization; diffusion; reassociation; and desorption. Within the metal, $H_2$ loses its electron to the palladium structure and diffuses through the membrane as a proton. At the exit surface the reverse process occurs. The trace components including $NH_3$, $H_2S$, and $HCl$ in biogas could potentially poison the precious metal components in the $H_2$ separation membrane and significantly reduce the membrane performance and stability. Microporous $SiO_2$ membranes have shown high selectivity and permeability for $H_2$ at close to ambient temperature.

While recent research has reported on biohydrogen production from liquid organic substrates in pure and sterile forms, embodiments of the present invention preferably comprise an apparatus and method to produce hydrogen from solid biological material, such as organic solid wastes (OSWs) or the like. Unlike the inventions mentioned above, embodiments of the present invention preferably comprise an apparatus and method of anaerobic hydrolysis and fermentation, or a chemical conversion of carbohydrates into alcohols or acids in the absence of oxygen, in tandem with photofermentation, and comprising a gas-specific membrane. Embodiments of the present invention preferably comprise a single vessel design incorporating at least two steps, an anaerobic fermentation stage and a photofermentation stage, and preferably comprise a membrane, preferably a hollow fiber membrane, separating fluid or gaseous phases. Other embodiments of the present invention preferably comprise an apparatus and method comprising biological conversion of acids to a gas and a heat treatment to suppress methanogens.

Embodiments of the present invention preferably comprise a two-step process configuration for hydrogen production, preferably at room temperature, from biomaterials with the first step preferably comprising generating $H_2$ gas or other gases through anaerobic hydrolysis and fermentation and the second step comprising generating additional $H_2$ gas or other gases through photofermentation of the products of the first stage and stabilizing the waste.

For sustainable $H_2$ production, substrates should preferably be carbohydrates from renewable sources at sufficient concentrations requiring minimum pretreatment, and available throughout the year at low cost. Materials comprising OSWs meet these requirements, and may be ideal feedstocks for biohydrogen production from the standpoint of pollution prevention, economics, and sustainability. Cellulose, hemicellulose, and lignin are the primary components of plant cells, and are thus the primary components of OSWs such as biomass wastes, food wastes, and farm wastes. The conversion of cellulose and hemicellulose first to glucose and xylose, respectively, and then to hydrogen, therefore, is a rational and sustainable solution to abatement of pollution, depletion of fossil fuel reserves, and emissions of greenhouse gases.

Biohydrogen has recently been produced from liquid organic substrates in pure and sterile forms, but there is a need for producing biohydrogen from any kind of biomaterials, including solid biomaterials. Additionally, combining waste stabilization and $H_2$ production in this manner conserves limited resources and be a cost-effective and sustainable approach. Cattle manure is currently produced at a rate of $2.2 \times 10^4$ kg/yr/cow, which translates to a COD equivalent of $2 \times 10^{14}$ kg/yr. The current practice of applying the manure to the ground as a fertilizer runs in the face of new regulations that prohibit land application.

There is currently a need for an optimal process configuration for development of a dry digestion process, modifying anaerobic technology to produce hydrogen rather than methane. While methane generation from wastes is well understood and has been reported upon, embodiments of the present invention preferably generate gas by two processes in tandem, which has previously not been accomplished. Even though the viability of the two processes has been demonstrated individually, the present invention integrates the two for larger scale practical applications.

BRIEF SUMMARY OF THE INVENTION

Embodiments of the present invention preferably comprise a system for producing a gas preferably comprising a multi-stage reactor preferably comprising at least one leach-bed reactor, at least one suspended-growth reactor, and a gas-specific membrane system preferably in fluid communication with the multi-stage reactor. The suspended-growth reactor is preferably in fluid communication with the leach-bed reactor. The suspended-growth reactor preferably comprises a continuous stirred-tank reactor. The multi-stage reactor preferably comprises a plurality of tubes, where the tubes are preferably perforated. The gas-specific membrane system preferably comprises ruthenium, nickel, alumina, or alumina composite. The gas-specific membrane system preferably comprises a hydrogen-selective membrane. The suspended-growth reactor preferably comprises a light source. The suspended-growth reactor preferably further comprises a magnetic stirrer. The leach-bed reactor preferably comprises a fixed-bed reactor.

Embodiments of the present invention preferably comprise a method for producing gas preferably comprising the steps of anaerobic hydrolysis-fermentation; photofermentation; removing the gas; and maintaining pH. The anaerobic hydrolysis-fermentation and photofermentation may occur in tandem. The anaerobic hydrolysis-fermentation preferably comprises percolating leachate in cross flow mode. The anaerobic hydrolysis-fermentation preferably comprises anaerobically fermenting leachate preferably at room temperature to preferably produce gas (e.g. hydrogen gas), carbon dioxide, and fatty acids. The photofermentation preferably comprises converting fatty acids to preferably produce gas (e.g. hydrogen), carbon dioxide, and organic residue. The anaerobic hydrolysis-fermentation and photofermentation preferably occur at room temperature. Maintaining pH preferably comprises monitoring and controlling different pH levels in different stages. Hydrogen partial pressure is preferably maintained and product inhibition is preferably avoided by preferably rapidly and efficiently separating the gas. Anaerobic hydrolysis-fermentation preferably occurs in a leach-bed reactor. Photofermentation preferably occurs in a suspended-growth reactor stage. Anaerobic hydrolysis-fermentation preferably comprises fermenting a biomaterial. The biomaterial is preferably a solid. Anaerobic hydrolysis-fermentation and photofermentation preferably comprise utilizing naturally occurring organisms in manure.

BRIEF DESCRIPTION OF THE SEVERAL VIEWS OF THE DRAWINGS

The accompanying drawings which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF PREFERRED EMBODIMENTS OF THE INVENTION

Figure 1:
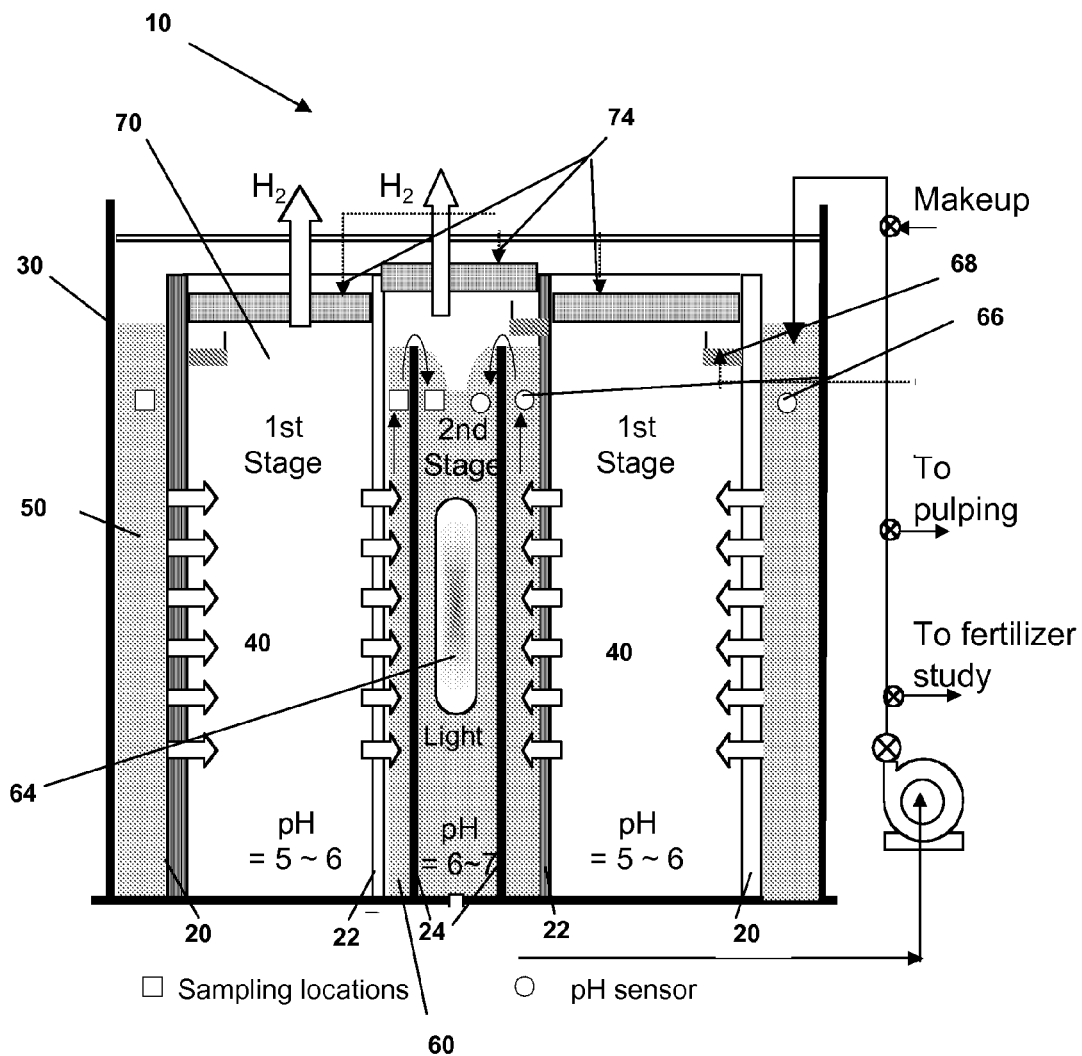
FIG. 1 is a schematic of a reactor illustrating an embodiment of the present invention.

Details of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

An embodiment of the present invention preferably comprises a reactor comprising: hydrogen selective separation membranes that maximize hydrogen production from OSWs; microbial populations and metabolisms in a biological hydrogen production process; a membrane system for hydrogen separation and purification; a refined model for hydrolysis/acidogenesis integrated with a logistic growth model for photofermentation to formulate and validate a complete model for biological hydrogen production; and optimal parameters and operating conditions to maximize hydrogen production. Acidogenesis comprises a biological reaction where simple monomers are converted into volatile fatty acids.

The present invention comprises a reactor for integrating anaerobic fermentation and photofermentation to produce hydrogen from solid organic wastes. Hydrogen generation by the two processes preferably occurs in tandem. Hydrogen partial pressure (e.g. <2,000 Pa) is maintained by incorporating a hydrogen selective membrane for efficient removal of hydrogen. Product inhibition is preferably avoided by incorporating a hydrogen selective membrane for efficient removal of hydrogen. A different pH for the two stages is maintained by two-stage reactor configuration with individual pH control. Substrate inhibition is avoided by flexibility to adjust recycle rate. High cell concentration for anaerobic fermentation is preferably maintained by a fixed bed reactor for anaerobic fermentation. Low HRT for anaerobic fermentation is preferably maintained by a fixed bed reactor with recycling. Uniform and optimal light intensity is preferably maintained by a suspended growth reactor for photofermentation. In a suspended growth reactor the biomass is preferably suspended in the liquid being treated.

Abundant and low cost inocula is employed, preferably by utilizing naturally occurring organisms in cattle manure. The reactor size is minimized preferably by cross-flow configuration, with built-in illumination. The overall cost is minimized preferably by using end products as nursery pots and fertilizers, reusing effluent in pulping digested manure, and recycling effluent as fertilizer.

Embodiments of the present invention preferably relate to a method and apparatus comprising two-stage membrane-based production of gas, preferably hydrogen gas or other gas, from solid biological materials, preferably organic waste materials or other biomaterials, using fermentative and photosynthetic processes comprising microorganisms. Embodiments of the present invention preferably comprise a vessel, such as a reactor or other vessel, integrating a two-stage process comprising anaerobic hydrolysis and fermentation and photofermentation to produce gas, including but not limited to hydrogen gas, preferably from solid biological organic wastes, while suppressing methanogens and stabilizing wastes, and the second step generates additional hydrogen through photofermentation of the products of the first stage, as well as stabilizing the waste.

A support for the biomass preferably comprises a manure matrix. The anaerobic fermentor, comprising the apparatus for anaerobic hydrolysis and fermentation, preferably comprises a leach-bed configuration, with the leachate preferably percolating in cross flow mode to maximize the hydrolysis and acidogenesis processes. A leach-bed reactor configuration preferably comprises an efficient dry digestion process.

The photofermentation reactor preferably comprises a continuous stirred-tank reactor (CSTR) configuration to maximize the light transmission for the phototrophic process. Gas, including but not limited to hydrogen, is preferably selectively harvested from both stages. Another embodiment of the present invention preferably comprises a flat panel reactor for larger scale, outdoor application.

An embodiment of the present invention preferably comprises a method of hydrolysis-acidogenesis in leach-bed reactors for the first stage that is preferably coupled to a second stage comprising a suspended growth reactor, comprising a logistic growth model for photofermentation in the second stage. Methane formation is preferably suppressed in a first stage by inhibiting methanogens, preferably by heat-shocking anaerobic sludge to inhibit methane-forming species, maintaining a low hydrogen partial pressure preferably by using hydrogen-selective membranes in the head space, maintaining a low hydraulic detention time, and maintaining a pH less than approximately 5.0. Photofermentation is preferably accomplished by maintaining a pH from approximately 6.0 to 7.0.

An embodiment of the present invention preferably comprises a process overview resulting in combustion of hydrogen to produce water, with an energy conversion efficiency of hydrogen of approximately 55%, and a net yield of 12 moles of hydrogen, or 3,432 kJ. The process comprises anaerobic fermentation, where:

$$C_6O_6H_{12}(glucose)+2H_2O=2CH_3COOH(fatty\ acid)+4H_2(g)+2CO_2(g)$$

and photofermentation, where:

$$2CH_3COOH+4H_2O=8H_2(g)+4CO_2(g)$$

resulting in:

$$C_6O_6H_{12}(glucose)+6H_2O=12H_2(g)+6CO_2(g).$$

An embodiment of the present invention preferably comprises a unique membrane that rapidly removes biogases and efficiently separates out high-purity hydrogen. Embodiments of the present invention preferably comprise hydrogen-specific membranes that resolve technical problems in converting wastes to hydrogen by alleviating process feed-back inhibition, preventing conversion and consumption of hydrogen, and concentrating and purifying the gas product. Thus, the conversion of solid waste into a value-added energy-efficient fuel, as well as nursery pots that can be produced from digested residues, addresses current waste-management problems in diverse, economically important industries, including but not limited to the dairy and food industries.

A preferred embodiment of the present invention preferably removes hydrogen gas from the bioreactor preferably by using a unique hydrogen-selective composite membrane, preferably comprising aluminum oxide as a substrate. Embodiments of the present invention preferably comprise a separation layer comprising a ruthenium-nickel thin film acting as a catalyst for hydrogen oxidation. Other embodiments of the present invention preferably comprise a microporous silicon dioxide matrix.

FIG. 1 illustrates an embodiment of the present invention comprising reactor 10. Reactor 10 comprises tube 20, tube 22, and tube 24 disposed concentrically inside tank 30. Feedstock, preferably comprising wet cattle manure, 40, is placed in annular space 60 between tube 20 and tube 22, both preferably perforated. Leachate 50 percolates from tank 30 radially through tube 20, through feedstock 40 and into annular space 60 between tubes 22 and 24. Thereafter, leachate 50 overflows into tube 24, where it is isolated from acid producing phase 40, so that optimal pH can be maintained for each phase. Light source 64 is placed at the center of tube 24. This configuration enables dry digestion under controlled moisture content. Anaerobic fermentation (hydrolysis and acidogenesis) occurs in annular space 60 between tube 22 and tube 24, producing $H_2$, $CO_2$ and dissolved fatty acids. Leachate 50 carries the dissolved volatile acids into the second stage in tube 24, where photofermentation takes place with the production of $H_2$ and $CO_2$. The two stages are fitted with pH monitors/controllers 66 to maintain optimal pH in each stage. A fraction of the effluent is preferably recycled to the first stage. Carbon dioxide in headspace 70 is preferably absorbed (e.g. with 50% KOH traps 68). Mixing in the second stage is preferably provided by stirrer (e.g. magnetic stirrer 72). Membranes 74 in the two stages enable hydrogen levels to be maintained at a specified pressure.

Thermodynamically, optimal hydrogen production by anaerobic fermentation with acetate as the end-product is realized only when hydrogen partial pressure in headspace 70 is maintained less than approximately 2,000 Pa. Accumulation of hydrogen in headspace 70 can cause product inhibition. Efficient removal of hydrogen is efficiently removed from headspace 70 for continuous hydrogen production.

Embodiments of the present invention preferably comprise an apparatus for gas separation, preferably hydrogen-selective membranes, preferably comprising Ru—Ni/γ-Al$_2$O$_3$/α-Al$_2$O$_3$ composites, microporous SiO$_2$ composites, and hollow fiber membranes. Biogas generated in the fermentation reaction comprises trace amounts of CH$_4$, NH$_3$, HCl, H$_2$S, so the hydrogen separation membrane preferably tolerates these trace gas components. This requirement excludes the use of palladium and palladium alloy membranes because these precious metals are prone to attack by the acid gases. Ru—Ni/γ-Al$_2$O$_3$/α-Al$_2$O$_3$ composite membranes comprise α-Al$_2$O$_3$ substrates to provide mechanical strength, and comprise γ-Al$_2$O$_3$ to provide a transitional layer between a separation layer and a macroporous substrate. The Ru—Ni/γ-Al$_2$O$_3$/α-Al$_2$O$_3$ composite membranes preferably comprise a separation layer of Ru—Ni. A transitional layer significantly reduces the thickness of the separation layer and enhances permeability and stability.

Embodiments of the present invention preferably comprise a catalytic membrane and method for optimum proton generation and rate of diffusion. An embodiment of the present invention comprise Ru—Ni membranes comprising catalytic properties that facilitate characteristic hydrogen oxidation reactions that involve H$_2$ dissociative adsorption on and permeation through the Ru—Ni surface with both pure H$_2$ and gas mixtures comprising trace components in the biogas. Another embodiment of the present invention preferably comprises a membrane comprising microporous SiO$_2$ composite membranes preferably comprising an α-Al$_2$O$_3$ substrate to provide the mechanical strength, γ-Al$_2$O$_3$ to provide the transitional layer between the separation layer and the macroporous substrate, and a separation layer of microporous SiO$_2$. A sol-gel technique preferably prepares a top layer and a transitional layer. Pure H$_2$ and H$_2$ gas preferably permeate the composite membranes.

Another embodiment of the present invention preferably comprises a membrane comprising a commercial hollow fiber membrane preferably comprising an apparatus for separating biogas, especially for biohydrogen purification. The molar flow rate FH2 (mole/s) of H$_2$ through the membrane may be described by the transport equation $F_{H2}=B_H A_m(p''_f-p''_p)$ where $B_H$ is the permeance of the membrane, $A_m$ is the membrane surface, and $(p''_f-p''_p)$ is the difference in partial pressure between the feed side and the permeate side. The value of n is a function of membrane pore size and hydrogen transport mechanism.

An embodiment of the present invention comprises an integrated process of hydrogen production from particulate organic wastes including hydrolysis, acidogenesis, anoxygenic photosynthesis, and separation of hydrogen from biogases in order to produce biohydrogen.

Figure 2:
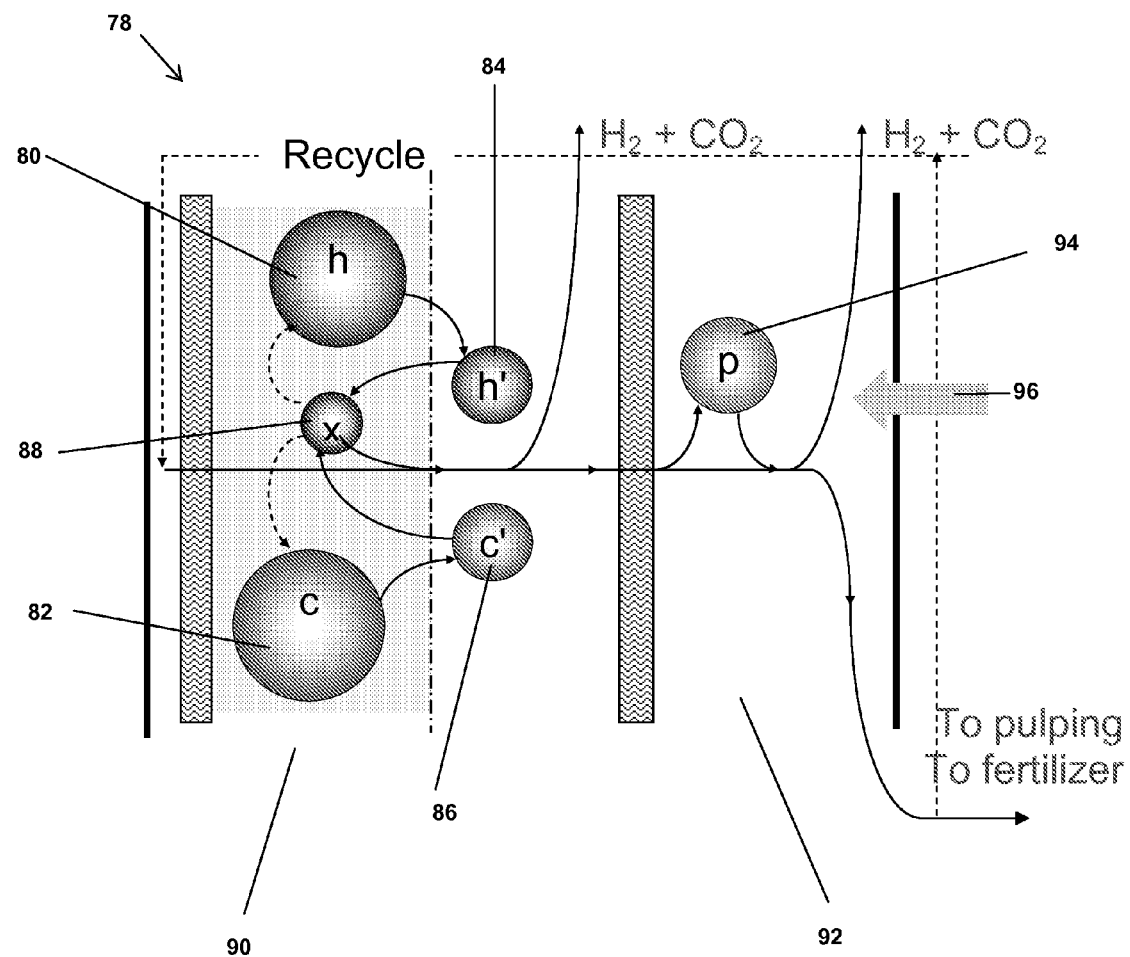
FIG. 2 is a computer-generated image of a schematic of the overview of the preferred embodiment of the method of the invention.

An embodiment of the present invention is illustrated in FIG. 2. Acidogenic bacteria 88 exist as a biofilm in manure matrix 78. The particulate degradable portion of cattle manure is comprised of hemicellulose 80 and cellulose 82. These two fractions are enzymatically hydrolyzed to their soluble hemicellulose 84 and soluble cellulose 86 and then degraded by acidogens 88 in first stage 90 at different rates, to produce fatty acids, $H_2$ and $CO_2$. The hydrolysis of hemicellulose 80, and of cellulose 82 are surface limiting reactions while the utilization of soluble hemicellulose 84 and of soluble cellulose 86 by acidogens 88 are a two-substrate-single-biomass. The fatty acids in the dissolved form flow from first stage 90 to second stage 92, where phototrophic bacteria 94 utilize them in the presence of light 96, to produce $H_2$ and $CO_2$.

An embodiment of the present invention comprises a downflow leach-bed reactor fed with cattle manure, modified for radial cross flow and utilizing a photosynthetic process and a membrane process. In addition, the present invention accommodates pH variation and speciation of volatile acids.

Figure 3:
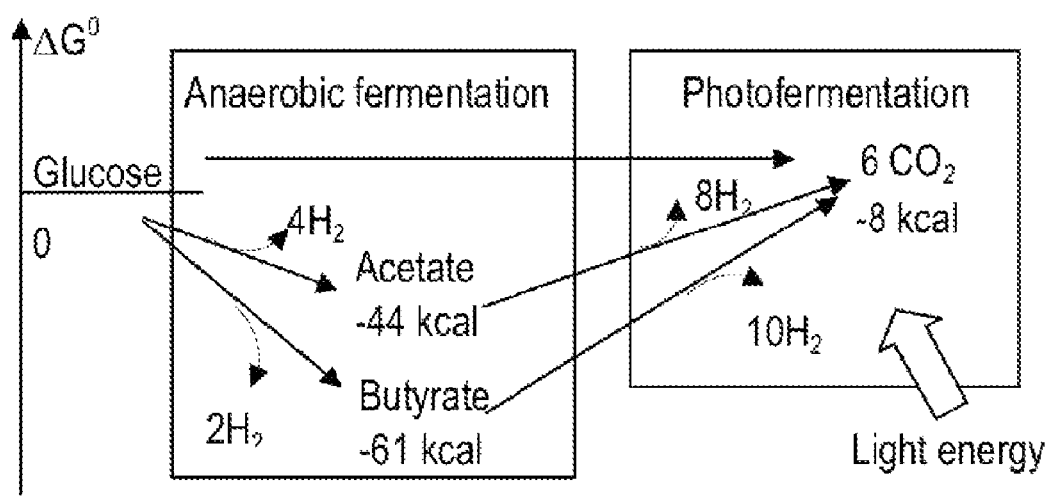
FIG. 3 is a diagram illustrating the energetics of a sequence of processes of an embodiment of the present invention.

Anaerobic fermentation followed by photofermentation of the products is an optimal process for producing $H_2$. This two-step configuration produces $H_2$ at a practical rate and economic yield with minimal energy needs, and at the same time, stabilizes wastes. Embodiments of the present invention comprise a substrate comprising biomass, and the $CO_2$ produced by this process is climate-neutral. Energetics of this sequence of processes utilizing glucose as the feedstock and acetate and butyrate as intermediate products are illustrated in FIG. 3.

Embodiments of the present invention comprise producing $H_2$ by fermentation of organics comprising cultures of *Enterobacter, Bacillus*, and *Clostridium*, of which, the latter have been found to yield the maximum yield of 1.6 to 2.36 M $H_2$/M glucose. Embodiments of the present invention comprise viable production of hydrogen using non-sterile feedstocks, comprising exploiting natural and/or abundant culture sources, such as soil micro flora or excess sludge from wastewater treatment plants. However, if mixed cultures from these sources are to be used, activity of hydrogen-consuming organisms (e.g. methanogens) found in those sources should be inhibited. Methods to inhibit methanogens include pretreatment of cultures and operating the reactor at short hydraulic retention times (e.g. approximately <8 hrs) and low pH (e.g. approximately 5 to 6.5). Two pretreatment methods reported to be effective in suppressing methanogens in the seed are acid-treatment and heat-treatment.

Embodiments of the present invention comprise generating volatile fatty acids by hydrolysis and acidogenesis in a leach-bed reactor at HRT of approximately 2 to 3 hrs and at pH approximately <5.5 using naturally occurring organisms in cattle manure residues. Embodiments of the present invention comprise inhibiting methanogenesis to levels of methane in the gas phase comprising less than approximately 1%. Embodiments of the present invention comprise using naturally occurring organisms comprise *Rhodobacter sphaeroides* for photofermentation in the second stage.

Embodiments of the present invention comprise a method to use cattle manure residues as feedstock in producing hydrogen through anaerobic fermentation followed by photofermentation. Cellulose, hemicellulose, and lignin are the primary constituents of cattle manure as well as many other solid biomaterials.

The invention is further described herein. While the preferred embodiment of the invention is directed to production of hydrogen gas from solid organic waste materials, the invention is also useful in any fuel derivation as appropriate using fermentative and photosynthetic microorganisms or their byproducts.

EXAMPLE 1

A mathematical model for the hydrolysis and acidogenesis reactions in anaerobic digestion/fermentation of cattle manure was performed. The particulate hydrolysable fraction of cow manure was composed of cellulose and hemicellulose that were hydrolyzed at different rates according to a surface-limiting reaction. The respective soluble products of hydrolysis were utilized by acidogens at different rates, according to a two-substrate, single-biomass model. Batch experimental results were used to identify sensitive parameters and to calibrate and validate the model. Results predicted by the model agreed well with the experimentally measured data not used in the calibration process. The correlation coefficient exceeded 0.91. The most significant parameter in the hydrolysis-acidogenesis phase was the hydrolysis rate constant for the cellulose fraction.

A two-substrate, single-biomass model was developed for the hydrolysis/acidogenesis phase and was validated using experimental batch data. A sensitivity analysis of the model parameters was performed. A two-phase reactor system was developed for dry digestion of cattle manure residues, with a leach-bed reactor comprising the first stage and a suspended growth reactor comprising the second stage. Chemical oxygen demand (COD) generation was optimized by enhancing hydrolysis and acidogenesis and minimizing methanogenic activity by maintaining pH below 5.5.

During dry digestion of cattle manure residues in a leach-bed reactor, substrate degradation curves exhibited two distinct segments. This observed two-segment profile was due to two components of cattle manure, a readily degradable faction, hemicellulose, and a slowly degradable fraction, cellulose. Different hydrolysis parameters and biokinetic parameters were found for the two components. Two enzymatic mechanisms were found: one mediated by native organisms found in manure residues and the other mediated by either external enzymes or by seed cultures that were added to the reactor to augment the hydrolysis process.

In the first mechanism, native organisms grew as colonies attached to particles in the solid matrix. The rate of hydrolysis by these organisms was dependent on the surface area of the particles occupied by the organisms. When the surfaces of the particles were fully saturated by the organisms, the rate was first order with respect to biomass concentration. In the two-substrate, single-biomass model, the hydrolysis step was modeled as a surface-limiting reaction. In the second mechanism, an initial concentration-dependent conversion factor was modeled. Cellulose was hydrolyzed by a family of enzymes, cellulase. Seed cultures were used to augment hydrolysis. The pH remained below 6.0 and had no effect on the hydrolysis rate.

Acidogenesis was subsequently modeled. The acidogenic biomass grew on the soluble products of hydrolysis consisting of a readily degradable component, hemicellulose, and a slowly degradable component, cellulose. The growth of acidogenic biomass was modeled as a single biomass (acidogens) feeding on two non-inhibitory substrates (soluble hemicellulose and soluble cellulose) with different biokinetic constants. The model formulation involved hydrolysis process parameters and biokinetic parameters. The parameters were established following a curve-fitting process using experimental data from a batch reactor run without any supplement. Experimental data from two batch reactors with various doses of heated anaerobic sludge added as a supplement were then used to validate the model using parameters estimated from another reactor.

Batch experiments were conducted in three 600 mL glass bottles (reactors), each in duplicate. Manure samples were gathered at a nearby dairy farm from a pile under the separator that is used to separate the manure from manure slurry resulting from the cleaning of farm houses with running water. Average age of the samples in the piles was two days. Equal amounts of manure sample were placed in each of the six reactors and filled with equal volumes of water. Reactor 1 did not receive any external supplements. Reactors 2 and 3 were seeded with different amounts of heat-treated anaerobic sludge from a wastewater plant. Heat treatment was conducted to suppress the growth of methanogens.

Table 1 summarizes the initial concentrations of acidogens, particulate hemicellulose, and particulate cellulose per gram of manure. The initial concentration of acidogen biomass was estimated from data reported in the literature. Initial concentrations of dissolved COD, which resulted from hemicellulose and cellulose after adding water, are also shown in Table 1. The pH remained below 6 throughout the tests. Methanogens have negligible activity at pH less than 6.0, thus the dominant processes occurring in the test reactors was hydrolysis and acidogenesis.

All variables are expressed in chemical oxygen demand (COD) basis. The probability that the regression coefficient would be as extreme as reported is p, $P_c$ is the concentration of cellulose in particulate form (g COD/g manure), $P_h$ is the concentration of hemicellulose in particulate form (g COD/g manure). $P_i$ is the concentration of component i in particulate form (g COD/g manure). $P_{i,0}$ is the initial concentration of component i in particulate form (g COD/g manure), $P_{t,0}$ is the initial concentration of total components in particulate form (g COD/g manure), $S_c$ is the concentration of cellulose in dissolved form (g COD/L), $S_h$ is the concentration of hemicellulose in dissolved form (g COD/L), X is the concentration of acidogenic biomass (g COD/g solids), a is the solubilization rate of enhancer (g COD/g manure-day), $a_c$ is the biomass yield coefficient with cellulose as substrate (g COD/g COD), $a_h$ is the biomass yield coefficient with hemicellulose as substrate (g COD/g COD), $C_e$ is the specific COD conversion rate of enhancers (g COD/g enhancer-day), EMR is the enhancer-to-enhancer ratio (g enhancer/g manure), $k_c$ is the maximum soluble substrate utilization rate of cellulose (1/day), $k_h$ is the maximum soluble substrate utilization rate of hemicellulose (1/day), $k_d$ is the biomass death rate (1/day), $K_{1i}$ is the hydrolysis rate constant for component i (1/day or g/g biomass-day), $K_{1s,i}$ is the half-saturation coefficient for hydrolysis of component i (g COD/g COD), $K_{sc}$ is the half-saturation coefficient for biomass uptake of cellulose (g COD/L), $K_{sh}$ is the half-saturation coefficient for biomass uptake of hemicellulose (g COD/L), and MLR is the manure-to-liquid ratio (g manure/L. water). $K_{1s,i}$, $K_{1i}$ are hydrolysis process parameters and $k_c$, $k_h$, $K_{sc}$, and $K_{sh}$ are biokinetic parameters.

TABLE 1

| Reactor contents | | | |
|---|---|---|---|
| Description | Reactor 1 | Reactor 2 | Reactor 3 |
| Amount of wet cattle manure (g) | 120 | 120 | 120 |
| Moisture content in wet cattle manure (%) | 77.5 | 77.5 | 77.5 |
| Amount of seed added, dry (g) | 0.00 | 4.85 | 7.28 |
| Initial concentration of biomass (g COD/g manure) | 0.035 | 0.035 | 0.035 |
| Initial concentration of hemicellulose (g COD/g manure) | 0.42 | 0.42 | 0.42 |
| Initial concentration of cellulose (g COD/g manure) | 0.41 | 0.41 | 0.41 |

TABLE 1-continued

| Reactor contents | | | |
|---|---|---|---|
| Description | Reactor 1 | Reactor 2 | Reactor 3 |
| Initial COD concentration which hydrolyzed from hemicellulose (g COD/L) | 0.83 | 0.87 | 0.88 |
| Initial COD concentration hydrolyzed from cellulose (g COD/L) | 0.82 | 0.84 | 0.85 |
| Total water (L) | 0.523 | 0.528 | 0.532 |
| Seed-to-manure ratio SMR (g/g) | 0.00 | 0.18 | 0.927 |
| Dry manure-to-liquid ratio MLR (g/L) | 51.68 | 51.15 | 50.90 |

Yield coefficients for acidogenic growth on soluble hemicellulose and cellulose were established based on studies on similar substrates. Based on a sensitivity analysis, when the yield was changed by a factor of two, the variation in the COD values predicted was less than 10% of the measured value. Thus, the yield values were set at 0.084 and 0.042 g COD of VSS/g COD, respectively. Specific COD conversion rates, $C_i$, were determined by fitting predicted COD data to experimentally measured COD data from Reactor 2. A correlation coefficient >0.95 and p<0.005 were used as criteria to establish how good the fit was. This process yielded specific COD conversion rates of 0.15 g COD/g sludge for hemicellulose and 0.001 g COD/g sludge for cellulose. The four hydrolysis parameters ($K_{1h}$, $K_{1c}$, $K_{1sh}$, and $K_{1sc}$) and the four biokinetic parameters ($k_h$, $k_c$, $k_{sh}$, and $k_{sc}$) determined through curve fitting using measured data from Reactor 1, and validated with the laboratory data from Reactors 2 and 3 are listed in Table 2. The maximum hydrolysis rates, $K_1$ were established for the surface-limiting model (1.4. per day for hemicellulose and 0.09 per day for cellulose). The hydrolysis saturation constants, $K_{1s}$ were established to be 28 g COD/g COD for hemicellulose and 1.5 g COD/g COD for cellulose. $K_{1sh}$ and $K_{1sc}$ were the least sensitive of the eight parameters.

A new biokinetic model was used: $(dS_c/dt)_{uptake} = -k_c(S_c X/(K_{sc}(1+S_h/K_{sh}))+S_c)$ MLR. The maximum growth rate of acidogens $k_i$ was found to be 0.51 per day for soluble hemicellulose and 0.034 per day for soluble cellulose. The values for saturation constant $K_s$ were established as 15 g COD/L for hemicellulose and 100 g COD/L for cellulose.

Figure 4:
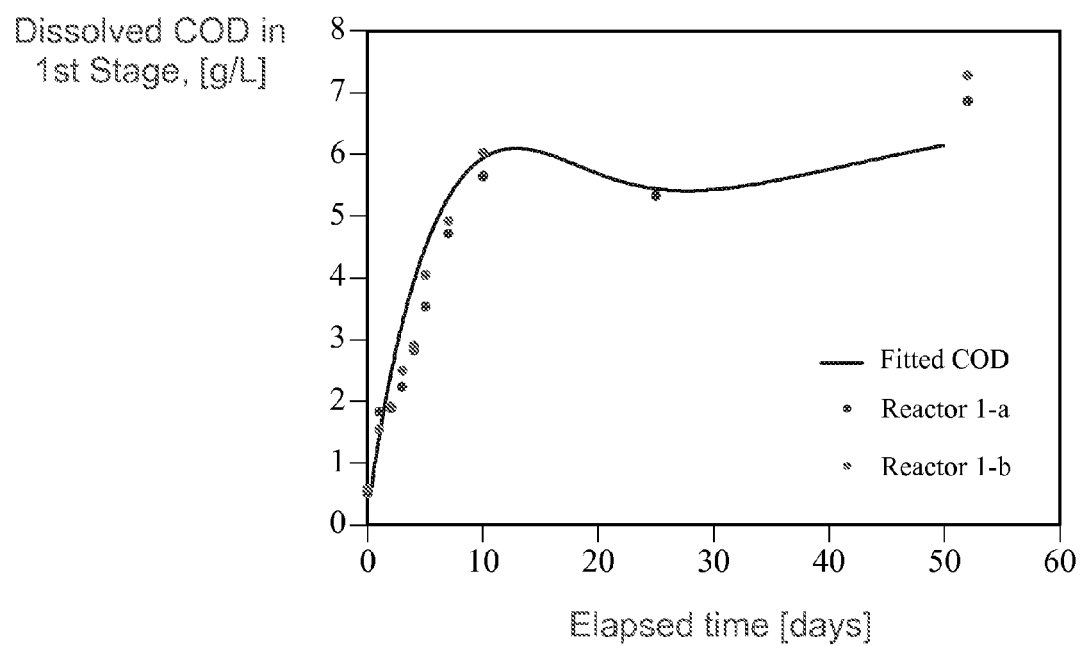
FIG. 4 is a computer-generated image graph of dissolved carbon oxygen demand (COD) over time.
Figure 5:
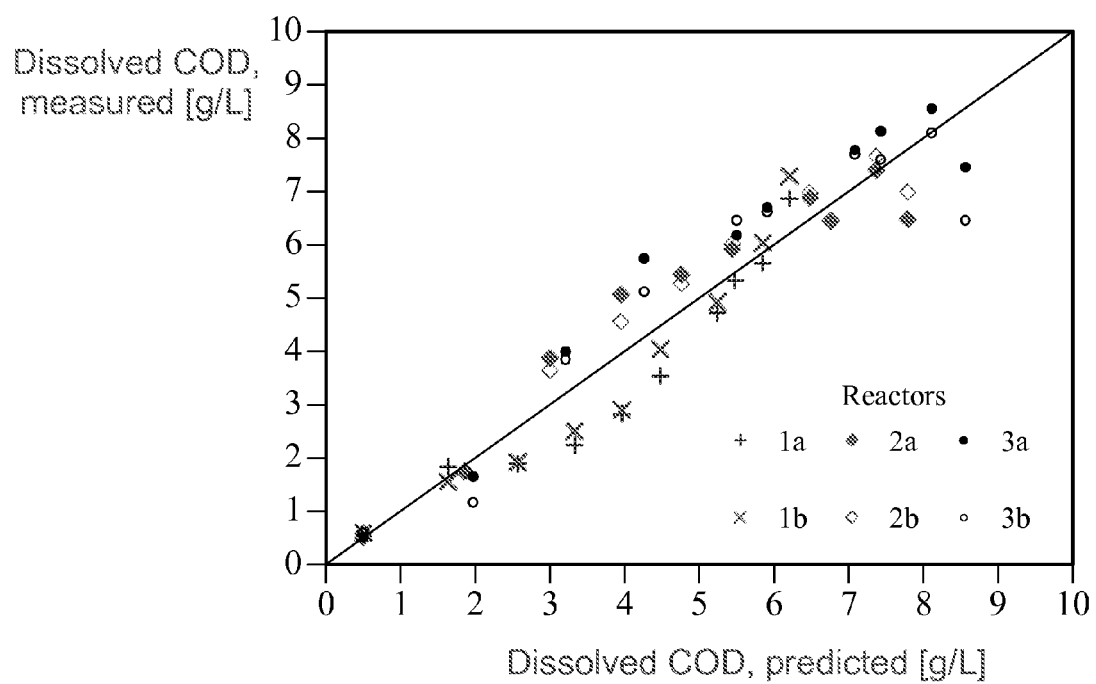
FIG. 5 is a computer-generated image graph of dissolved carbon oxygen demand (COD) (measured) versus dissolved COD (predicted)

COD values predicted by the model were compared against measuring data. FIG. 4 illustrates model predictions using the parameters found, closely following the temporal trend in the measured COD data from Reactor 1, which did not receive any supplement. Measured data from Reactors 2 and 3 that received seed supplement were used to further validate the model. The two variables that distinguish Reactors 2 and 3 from each other and from Reactor 1 are the seed-to-manure ratio and the manure-to-water ratio compiled in Table 4. FIG. 5 shows agreement between the COD predicted by the model and the measured COD values from the three reactors. The agreement between the predicted and measured COD values was statistically significant (p<0.005), individually for the three reactors (with $r^2$=0.980, 0.933, and 0.872, respectively) as well as for the three reactors together (with overall $r^2$=0.91 at p<0.002).

Figure 6:
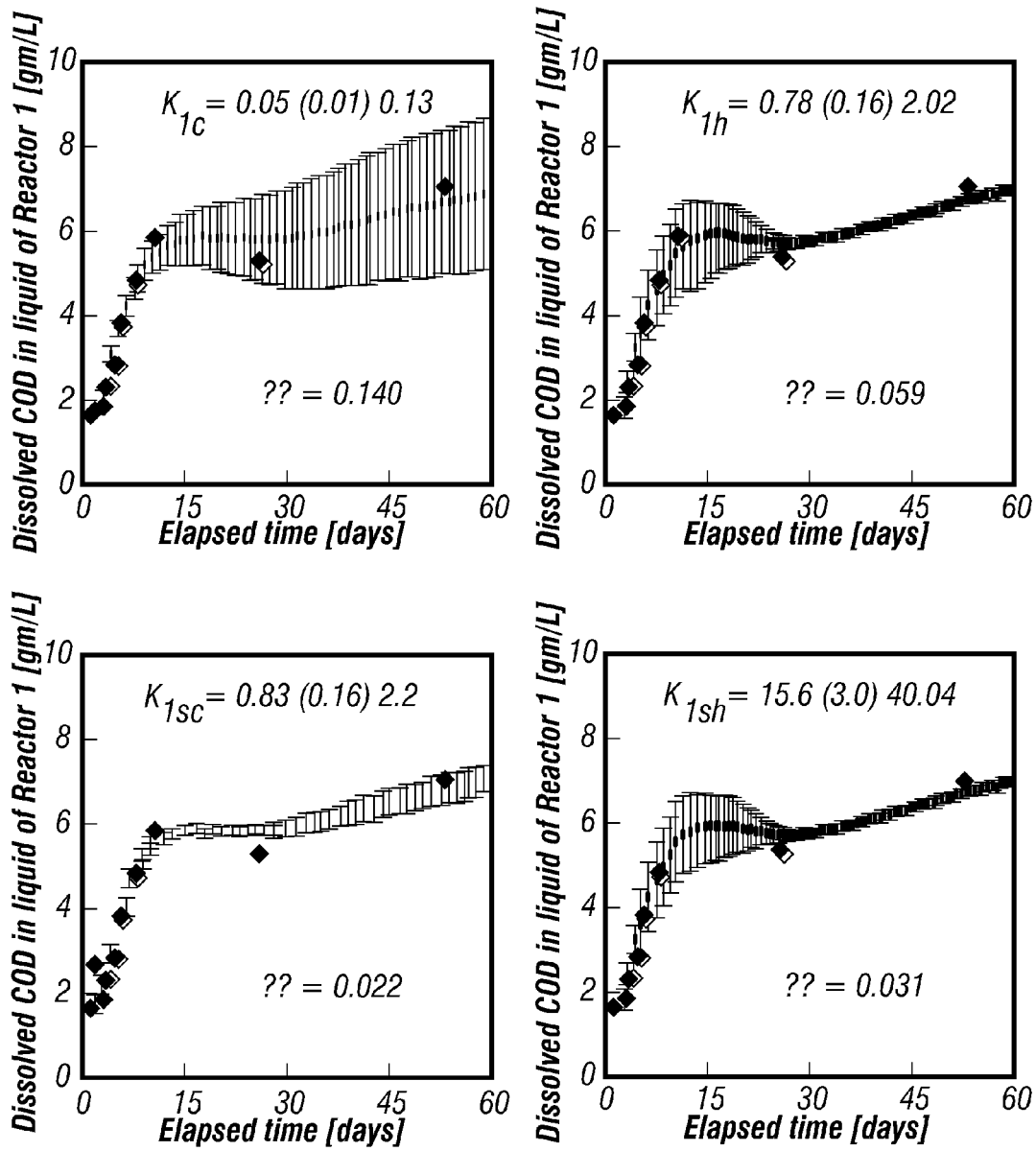
FIG. 6 is a computer-generated image graph of a compilation of COD mean profiles for eight parameters, including biokinetic coefficients and hydrolysis rate constants.
Figure 6:
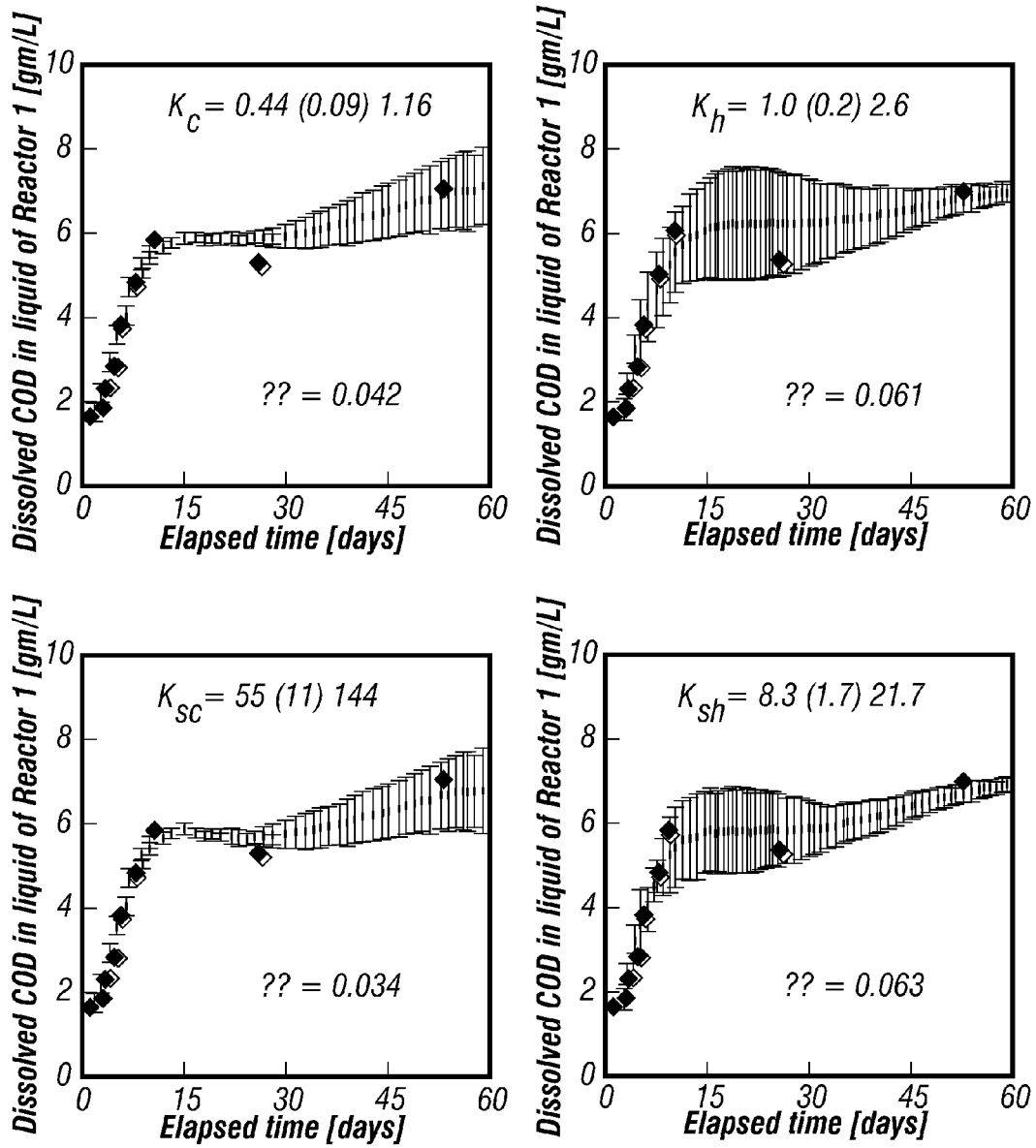

A sensitivity analysis was conducted to identify the most sensitive parameters in the hydrolysis-acidogenesis step. Nine COD profiles were generated and then combined to generate a mean profile with a spread of one standard deviation. A compilation of these mean profiles for each of the eight parameters is shown in FIG. 6, along with the measured COD data from Reactor 1. These plots indicate that the maximum hydrolysis rate constant $K_{1c}$ for cellulose to be highly sensitive, followed by the biokinetic coefficients $k_h$ and $k_{sh}$ for hemicellulose, to a lesser extent.

A two-substrate, single biomass model integrating hydrolysis and acidogenesis in anaerobic digestion of cattle manure was validated using batch experimental data. Hydrolysis was the rate-limiting step in the anaerobic digestion of complex particulate substrates and was used in designing, monitoring, analyzing, and optimizing the anaerobic gasification process.

TABLE 2

Model parameter output

| Model Parameters | Value at 37° C. | |
| --- | --- | --- |
| | Hemicellulose | Cellulose |
| Maximum rate of hydrolysis, $K_{1i}$ (day$^{-1}$) | 1.4 ± 0.13 | 0.09 ± 0.008 |
| Saturation constant for hydrolysis, $K_{1s\,i}$ (—) | 28.0 ± 2.52 | 1.5 ± 0.14 |
| Saturation constant for fermentation, $K_{s\,i}$ (g COD/L) | 15.0 ± 1.35 | 100 ± 9.0 |
| Maximum substrate utilization rate, $k_i$ (1/day) | 1.8 ± 0.16 | 0.80 ± 0.07 |

EXAMPLE 2

First-order, second-order, and surface-limiting reactions in anaerobic hydrolysis of cattle manure were evaluated. Laboratory batch experiments were conducted with cattle manure as the substrate to evaluate the three hydrolysis models and to validate the hydrolysis-acidogenesis model. Enhancement of hydrolysis by enrichment with enzymes was also investigated. Cellulase was used as an enhancer solely to validate the process model. Samples of cattle manure were obtained from a pile of dairy filtered manure wash. The age of the test samples in the pile was 2 days. The tests were conducted in batch mode in 600 mL glass bottles. Five batch reactors (labeled Reactor 1, 2, 3, 4, and 5) were run, each with a duplicate. Reactor 1 contained a raw manure sample, topped with water. Reactors 2 to 5 contained raw manure, enriched with different amounts of the cellulose enhancer and topped with water. Another set of experiments was conducted to verify that active hydrolytic organisms were already present in the manure samples. In these experiments, two 600-mL batch reactors (labeled Reactors 6 and 7) were run in duplicate. Both of those reactors were filled with raw manure samples and water; Reactor 7, however, was dosed with a biocide (1.9 g/L HgCl$_2$) to inhibit bacterial activity.

Three kinetic models were evaluated for suitability in describing anaerobic hydrolysis of particulate wastes. The three hydrolysis models evaluated were: a first-order reaction in particulate substrate concentration model, a second-order reaction in acidogenic biomass and particulate substrate concentrations model, and a two-parameter, surface-limiting reaction model. Process models incorporating the three hydrolysis reaction models were developed to describe the hydrolysis-acidogenesis phase in the fermentation of cattle manure.

Batch reactors were run with cattle manure as the substrate under five different conditions to calibrate and validate the process models. The two-parameter, surface-limiting reaction model and the single-parameter, second-order reaction model were found to fit the experimental results better than the simple first-order reaction model with r$^2$ values of 0.914, 0.913, and 0.881, respectively. The temporal COD solubilization curve consisted of two distinct segments. This is due to two distinct components of cattle manure: a readily hydrolyzable fraction composed primarily of hemicellulose and a slowly hydrolyzable fraction composed primarily of cellulose. These two fractions were identified as the major constituents of cattle manure, each wet waste. Naturally existing cellulolytic and hemicellulolytic organisms in cattle manure hydrolyzed the particulate forms of cellulose and hemicellulose contained therein.

The quantities of manure samples, water, cellulase enrichment, and biocide added to each reactor are shown in Table 3. All the reactors were placed in a water bath maintained at 37±2° C. Liquid samples from the reactors were withdrawn periodically to measure pH using a pH electrode probe. The samples were filtered with a 0.45 μm membrane filter and the COD of the filtrate was measured following Standard Methods 522D to determine dissolved COD.

TABLE 3

Contents of test reactors.

| Description | Reactor 1 | Reactor 2 | Reactor 3 | Reactor 4 | Reactor 5 | Reactor 6 | Reactor 7 |
| --- | --- | --- | --- | --- | --- | --- | --- |
| Amount of wet cattle manure (g) | 120 | 120 | 120 | 120 | 120 | 100 | 100 |
| Moisture content in wet manure (%) | 78.7 | 78.7 | 78.7 | 78.7 | 78.7 | 77.3 | 77.3 |
| Amount of cellulase added (g) | 0.00 | 0.05 | 0.10 | 0.15 | 0.20 | 0.00 | 0.00 |
| Amount of biocide added (g) | 0.00 | 0.00 | 0.00 | 0.00 | 0.00 | 0.00 | 1.00 |
| Water added to reactor (L) | 0.40 | 0.45 | 0.45 | 0.45 | 0.45 | 0.43 | 0.43 |
| Cellulase-to-manure ratio (mg/g) | 0.00 | 2.00 | 3.90 | 5.90 | 7.80 | NA | NA |
| Manure-to-liquid ratio (g/L) | 51.68 | 46.93 | 46.93 | 46.93 | 46.93 | 42.83 | 42.83 |

EXAMPLE 3

A hydrolysis-acidogenesis phase was modeled and was based on the simplifying assumptions that the particulate hemicellulose and cellulose fractions were hydrolyzed by acidogens; the acidogens grew attached to the solid matrix, utilizing the dissolved form of hemicellulose and cellulose as substrate; and the enhancers hydrolyzed the particulate hemicellulose and cellulose in proportion to their respective initial concentrations. The solubilization efficiency of the enhancer, cellulase, was estimated to be 15% through a curve-fitting process. A sensitivity analysis showed that the change in COD production was within 1% when the efficiency ranged from 10 to 20%. There was negligible methanogenic activity in the reactors. Thus, the only processes occurring in the reactors were hydrolysis and acidogenesis.

Figure 7:
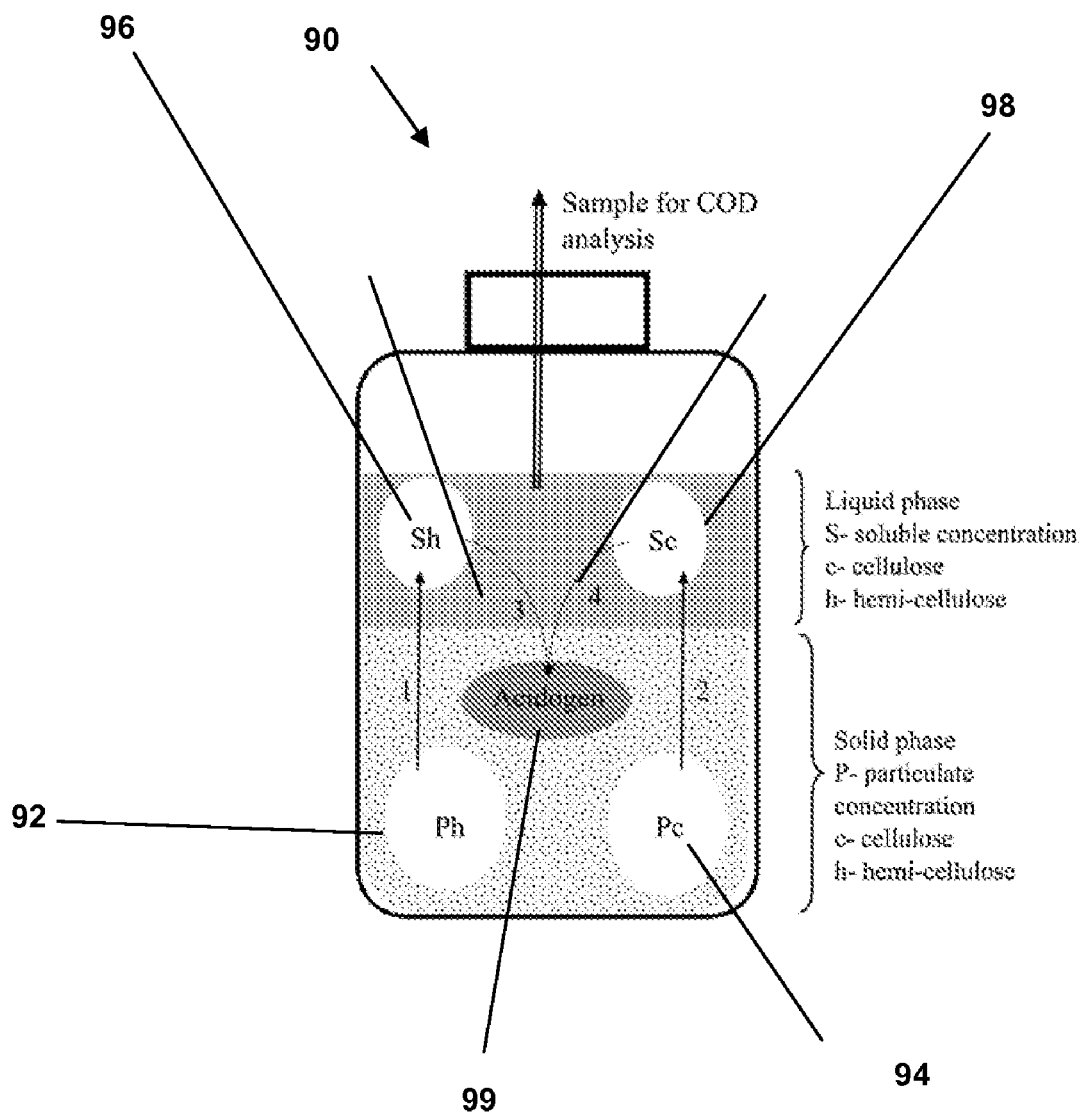
FIG. 7 is a drawing illustrating a conceptual model of a batch system.

The modeling framework incorporating these assumptions is illustrated in FIG. 7 illustrating a conceptual model of batch system 90 comprising hydrolysis 1 of particulate hemicellulose 92, hydrolysis 2 of particulate cellulose 94, biouptake 3 of soluble hemicellulose 96, and biouptake 4 of soluble cellulose 98 to acidogen 99. Based on the above assumptions, the rate of change of particulate species i (in the forms of hemicellulose 92 and cellulose 94) due to hydrolysis can be expressed as follows for the three hydrolysis reaction models:

The overall rate of the anaerobic process of gasification of particulate wastes by the above scheme is dependent on the rate limiting step comprising the hydrolysis step as the rate-limiting step. Hydrolysis reaction models for use in modeling the hydrolysis/acidogenesis step in the digestion of cattle manure are:

First-order reaction model:

$$dP_i/dt = -K_{1i}(P_i) - \alpha(P_{i,0}/P_{t,0})$$

Second-order reaction model:

$$dP_i/dt = -K_{1i}(P_i)(X) - \alpha(P_{i,0}/P_{t,0})$$

Surface-limiting reaction model (Contois kinetic model):

$$dP_i/dt = -K_{1i}(P_i/X/(K_{1si} + P_i/X))(X) - \alpha(P_{i,0}/P_{t,0})$$

In the above equations, the second term on the right-hand side represents the enhancement of hydrolysis by the cellulose enhancer where, $\alpha$ is the solubilization rate of the enhancer. While this term was zero for Reactor 1, for Reactors 2 to 5, $\alpha$ is expressed as $$\alpha = C_e \text{EMR}$$

where $C_e$ is the specific COD conversion rate of the enhancer (g COD/g enhancer-day) and EMR is the enhancer-to-manure ratio (grams enhancer/g manure). The specific COD conversion rate of cellulase was obtained from the supplier as 2.074 g COD/g cellulase-day.

Regardless of the hydrolysis reaction model, the utilization rates of dissolved hemicellulose and cellulose by the acidogenic biomass can be expressed as follows according to the two-substrate—one-biomass model:

Uptake rate of hemicellulose by acidogens:

$$(dS_h/dt)_u = -k_h(S_h X/(K_{sh}(1 + S_c/K_{sc})) + S_h) \text{MLR}$$

Uptake rate of cellulose by acidogens:

$$(dS_c/dt)_u = -k_c(S_c X/(K_{sc}(1 + S_h/K_{sh})) + S_c) \text{MLR}$$

Therefore, the net rate of change of dissolved species (i=hemicellulose or cellulose) in the reactor is:

$$(dS_i/dt) = -(dP_i/dt)\text{MLR} + (dS_i/dt)_u$$

Thus, the rate of change of dissolved COD in the reactor is:

$$d(COD)/dt = \sum_{i=c}^{i=h} (dS_i/dt)$$

The rate of growth of acidogenic biomass can be expressed as:

$$dX/dt = \sum_{i=c}^{i=h} [(dS_i/dt)a_i] - k_d X$$

where $a_i$ is the yield coefficient [—]; and $k_d$ is the death rate [1/day].

The model equations contain up to four hydrolysis process parameters ($K_{1h}$ and $K_{1sh}$ for hemicellulose and $K_{1c}$ and $K_{1sc}$ for cellulose) and four biological process parameters ($k_h$ and $K_{sh}$ for hemicellulose and $k_c$ and $K_{sc}$ for cellulose). Since these parameters were not measured through independent experiments, a curve-fitting process was used to estimate them. Measured COD data from Reactor 1 was used in the curve-fitting process to estimate the eight parameters, which were then validated using measured COD data from Reactors 2, 3, 4, and 5. The model equations were solved using a dynamic simulation program to generate the COD profile as a function of time.

The literature was surveyed to determine yield coefficients for acidogenic growth on soluble forms of hemicellulose ($a_h$) and cellulose ($a_c$). Since the substrates, experimental conditions, and the data analysis methods varied from study to study, it was not possible to reconcile and corroborate those values. Typical yield coefficients ranged as follows: 0.026 g COD of VSS/g COD for cattle manure wastewater, where VSS is Volatile Suspended Solids; 0.047 g COD of VSS/g COD for amino adds and sugars; 0.057 g COD of VSS/g COD for activated sludge; 0.051 g COD of VSS/g COD for molasses wastewater; and 0.100 g COD of VSS/g COD for with amino acid, sugars, and fatty acid. When comparing the three hydrolysis models, absolute values for the yield coefficients were not established; the same values were used for the three models, but of appropriate magnitude. The following values were used for the yield coefficients: 0.084 and 0.042 g COD of VSS/g COD, for $a_h$ and $a_c$, respectively.

EXAMPLE 4

Figure 8:
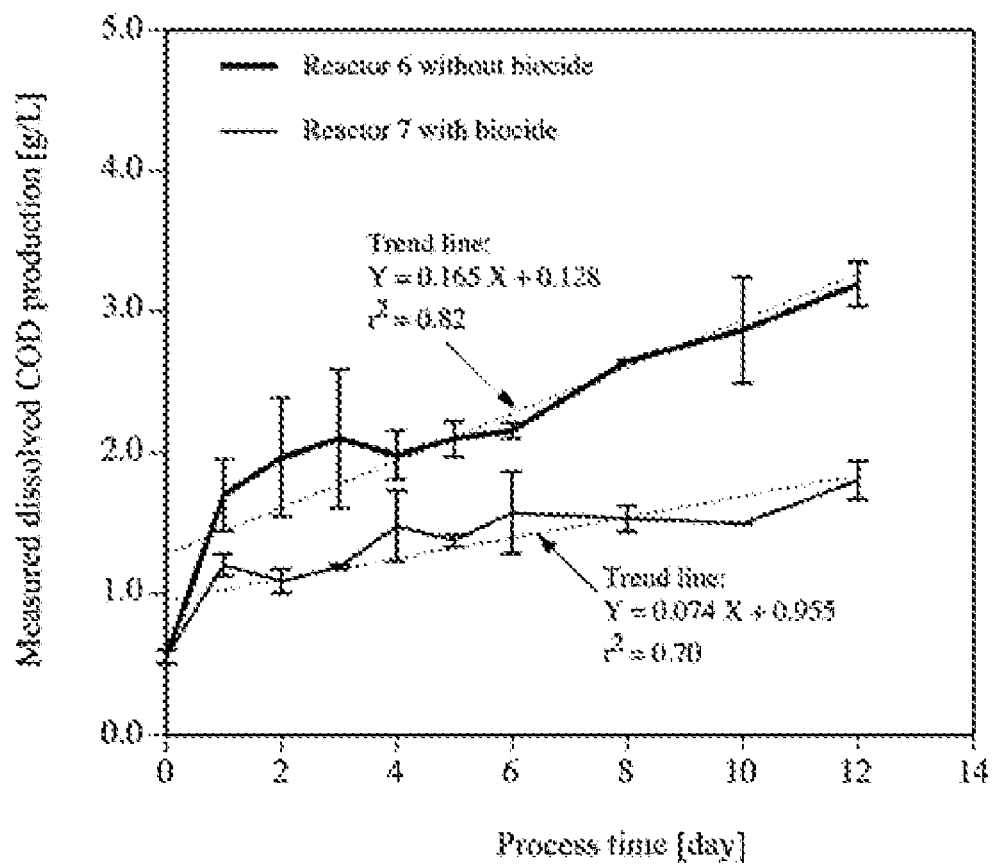
FIG. 8 is a computer-generated image graph illustrating comparisons of dissolved COD production with and without biocide.

Modeling assumptions were verified and model parameters were estimated, calibrated, and validated. FIG. 8 is an illustration of the impact of the biocide dose on dissolved COD production in Reactors 6 and 7. In Reactor 6, which was not dosed with the biocide, COD production continued to increase with time while COD production in Reactor 7, which was dosed with the biocide, was significantly lower. The slight increase in COD production in Reactor 7 was due to abiotic processes or inadequate biocide dosage. The production of dissolved COD was primarily due to active hydrolytic organisms naturally present in cattle manure.

Figure 9:
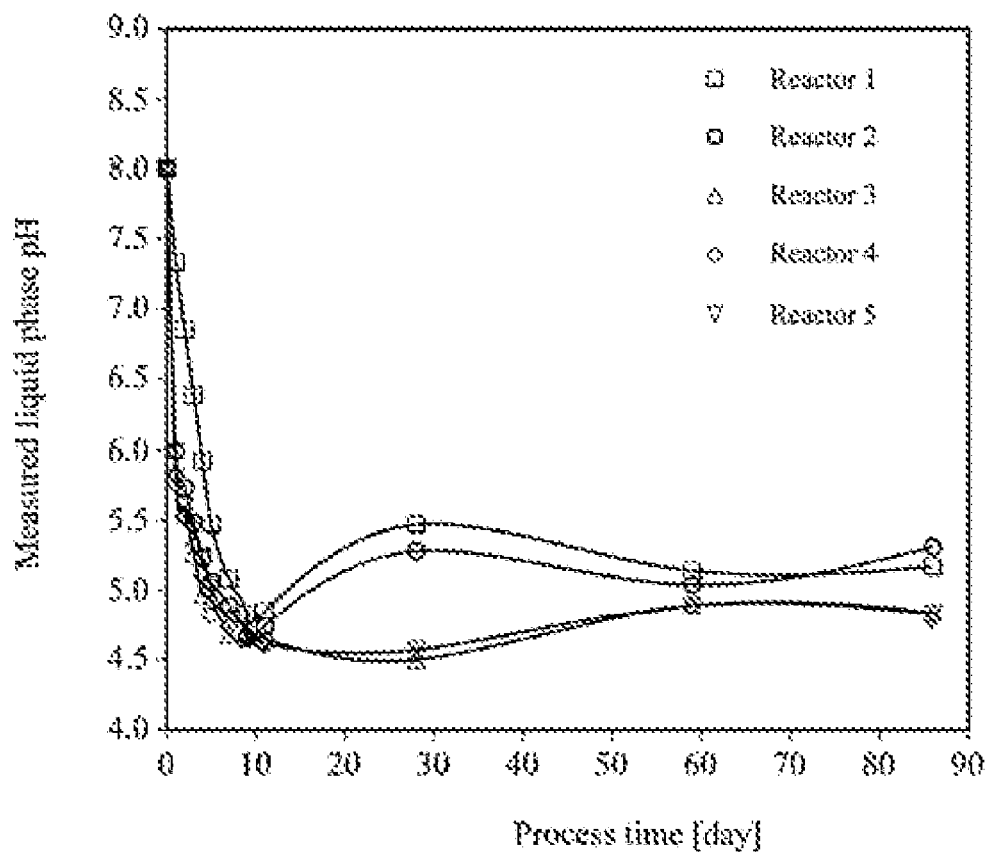
FIG. 9 is a graph illustrating average pH in the liquid phase in reactors.

FIG. 9 illustrates that the pH in all the reactors remained below 5.5. Methanogenic activity was negligible in this pH range and the only processes that occurred in the reactors were hydrolysis and acidogenesis.

Figure 10:
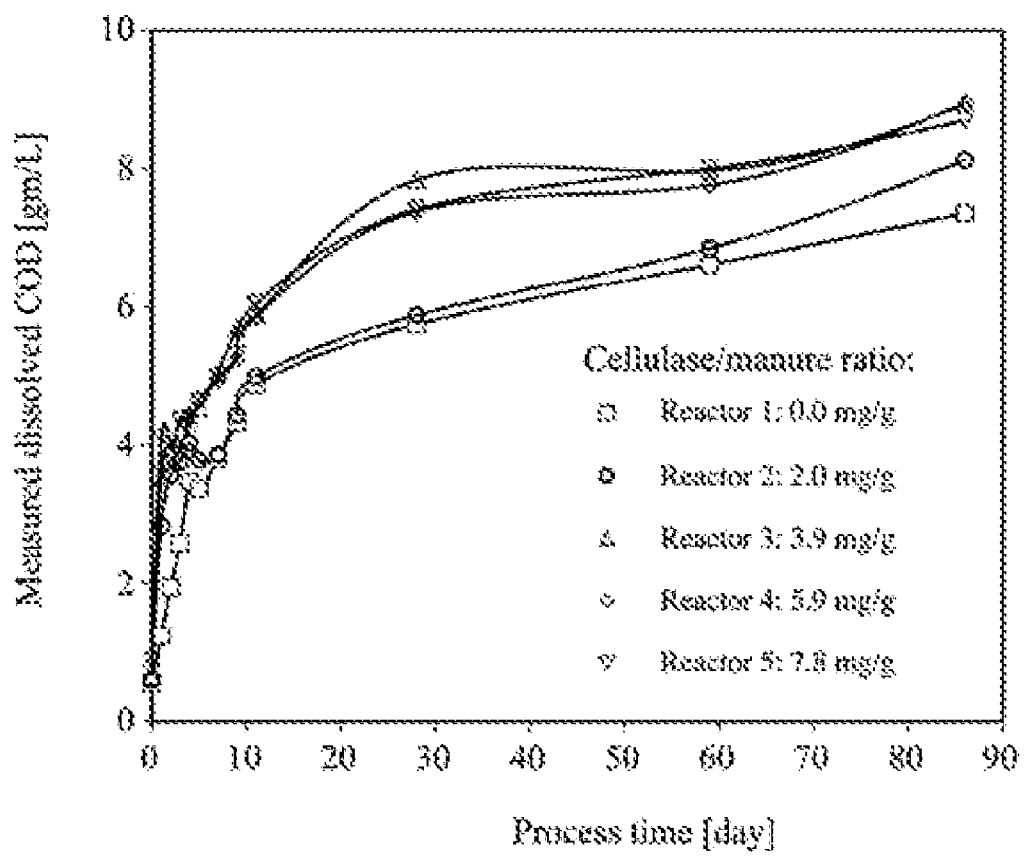
FIG. 10. is a graph illustrating enhancement of hydrolysis by cellulose.
Figure 11:
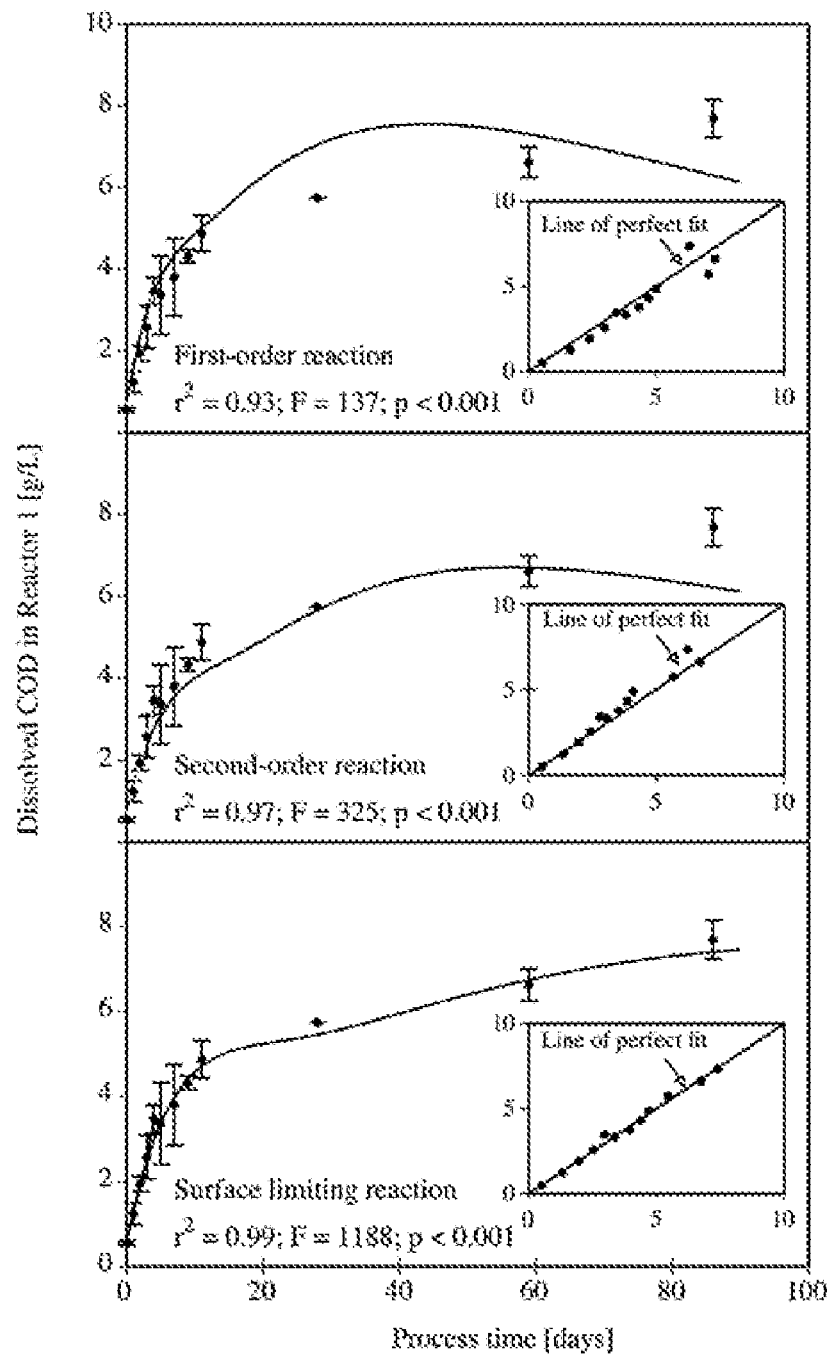
FIG. 11 is a graph illustrating a comparison of three hydrolysis models referencing Reactor 1 where each inset shows measured COD vs. predicted COD.
Figure 12:
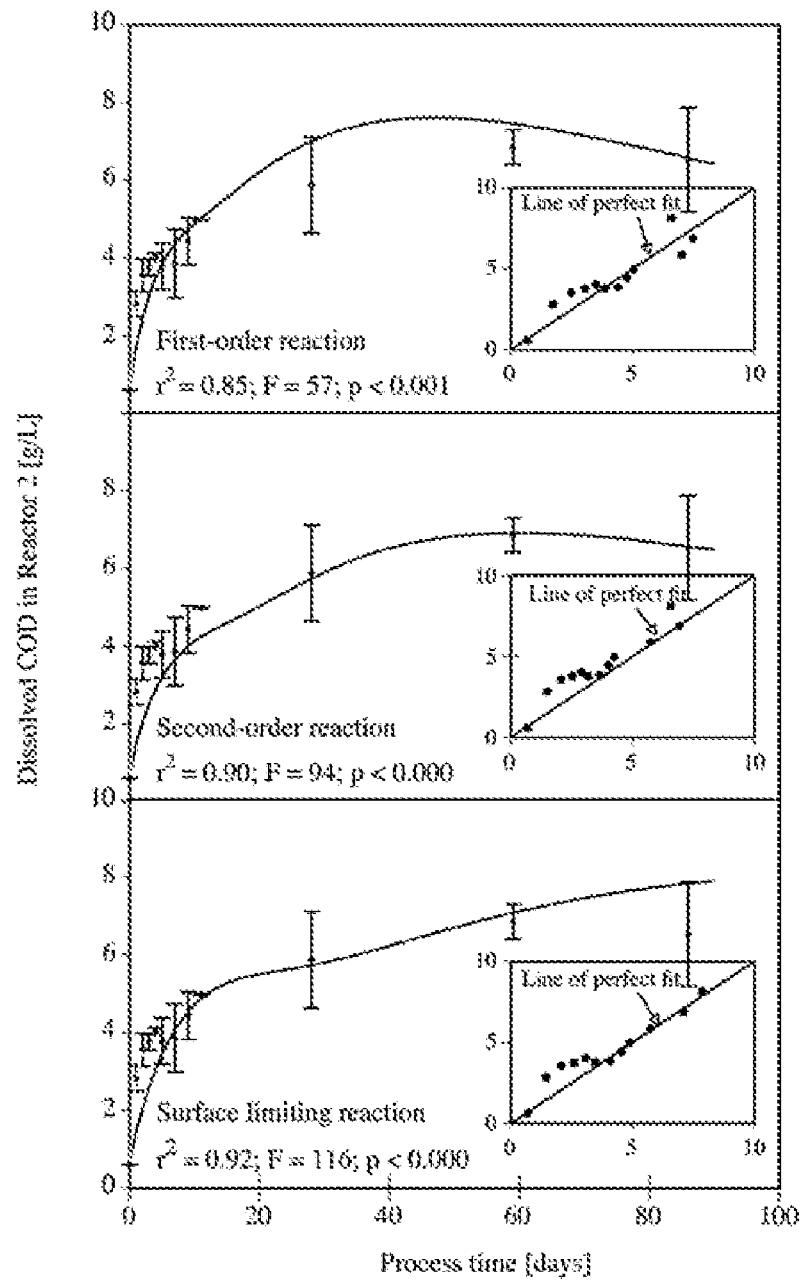
FIG. 12 is a graph illustrating a comparison of three hydrolysis models referencing Reactor 2 where each inset shows measured COD vs. predicted COD.
Figure 13:
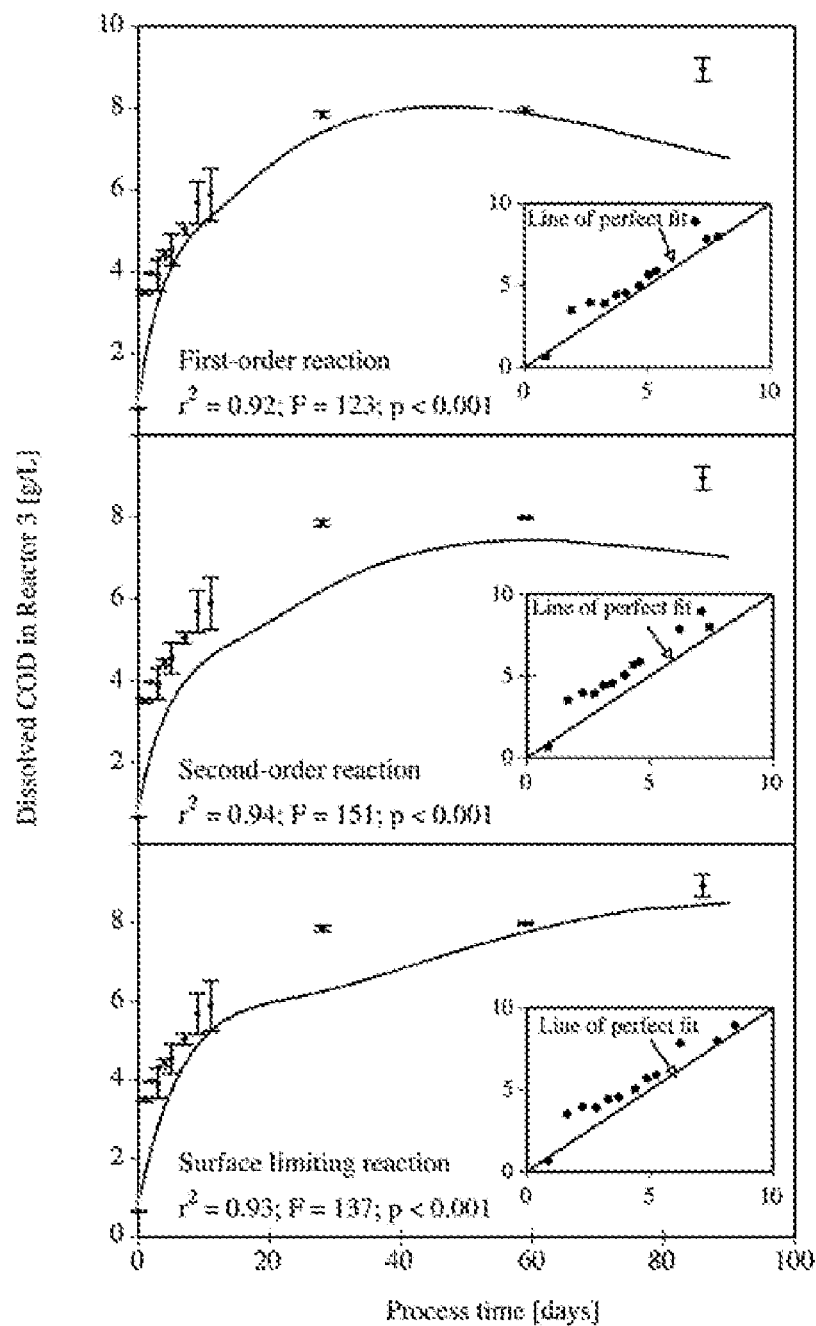
FIG. 13 is a graph illustrating a comparison of three hydrolysis models referencing Reactor 3, where each inset shows measured COD vs. predicted COD.
Figure 14:
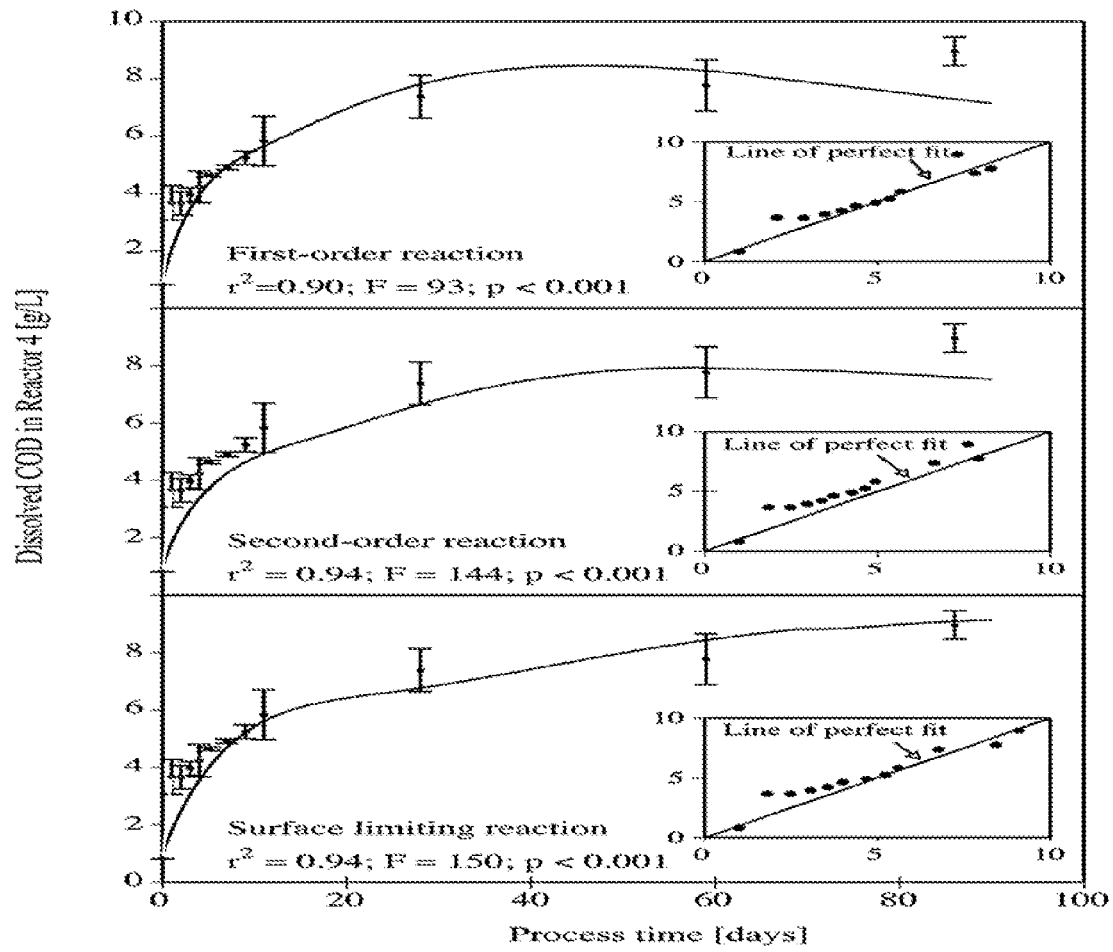
FIG. 14 is a graph illustrating a comparison of three hydrolysis models referencing Reactor 4, where each inset shows measured COD vs. predicted COD.
Figure 15:
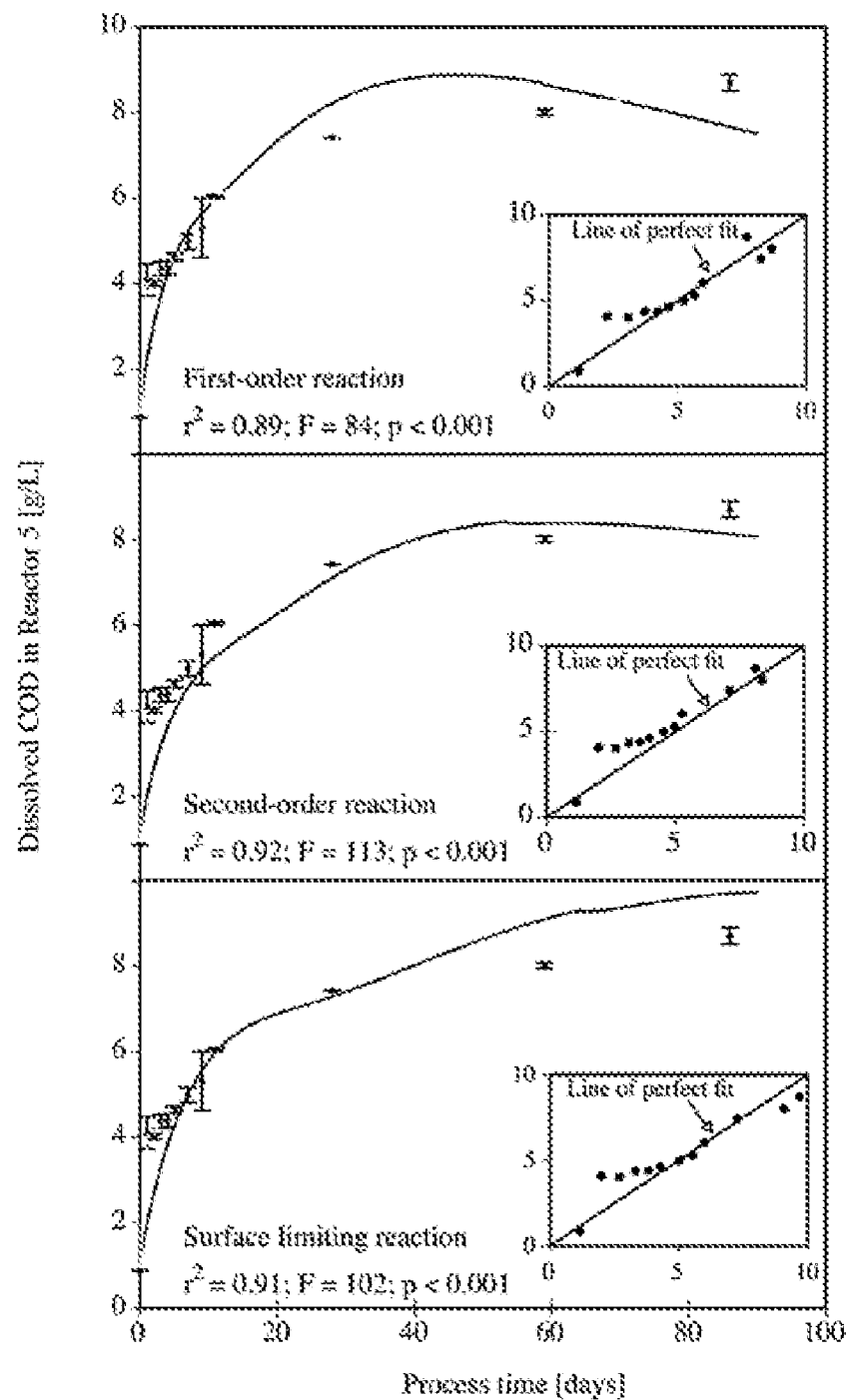
FIG. 15 is a graph illustrating a comparison of three hydrolysis models referencing Reactor 5, where each inset shows measured COD vs. predicted COD.

FIG. 10 is an illustration of the enhancement of the hydrolysis process as reflected by the increase in COD generation due to increasing doses of cellulase as the enhancer. COD generation increased 25 to 30% when the cellulase-to-manure ratio increased from 2 mg/g to 3.9 mg/g. However, further increase of cellulose-to-manure ratio up to 7.8 mg/g did not result in any increase in COD release due to saturation, due to mass transfer limitations in the hydrolysis step in this surface-limiting model.

The best-fit values for the eight parameters were found by a curve-fitting process to match the COD data measured in Reactor 1 that did not receive any enhancers. The best-fit parameters found for the three hydrolysis models are compiled in Table 4. The hydrolysis parameters are different for the three models as the underlying mechanisms are different. In the case of the biological parameters, the estimated $k_i$ values are comparable for the three models as expected; while the $K_{si}$ values are comparable for the first-order and second-order models, the corresponding values for the surface-limiting model are an order of magnitude higher.

TABLE 4

Best-fit values of model parameters.

| Parameter | First-order reaction model | Second-order reaction model | Surface limiting reaction model |
|---|---|---|---|
| For hemicellulose: | | | |
| $K_{1h}$ (day$^{-1}$) | 0.05 ± 0.006 | 1.2 ± 0.104 | 1.4 ± 0.12 |
| $K_{1sh}$ (—) | — | — | 28.0 ± 2.0 |
| $K_h$ (day$^{-1}$) | 1.0 ± 0.12 | 0.9 ± 0.078 | 1.8 ± 0.16 |
| $K_{sh}$ (g COD/L) | 2.2 ± 0.26 | 2.5 ± 0.22 | 15.0 ± 1.29 |
| For cellulose: | | | |
| $K_{1c}$ (day$^{-1}$) | 0.019 ± 2.28 | 0.28 ± 0.024 | 0.09 ± 0.008 |
| $K_{1sc}$ (—) | — | — | 1.5 ± 0.13 |
| $K_c$ (day$^{-1}$) | 0.75 ± 0.09 | 0.5 ± 0.044 | 0.8 ± 0.07 |
| $K_{sc}$ (g COD/L) | 75.0 ± 9.0 | 55.0 ± 4.8 | 100.0 ± 8.6 |

The parameters found through curve-fitting were further validated with COD data from Reactors 2, 3, 4, and 5 that received various doses of the enhancer. The COD profiles predicted by the three models for Reactors 2, 3, 4, and 5 agreed with the measured data as summarized in Table 5. The overall fit between COD measured experimentally and the COD predicted by the process model incorporating the three hydrolysis models was good ($r^2 > 0.85$ for 120 data points, with the probability of the correlation, $p < 0.001$). This model was valid and the observed two-segment COD profiles were due to the two components in cattle manure, i.e. hemicellulose and cellulose.

TABLE 5

Quality of Prediction of the three models.

| Model | | Reactor 1 | Reactor 2 | Reactor 3 | Reactor 4 | Reactor 5 | Overall |
|---|---|---|---|---|---|---|---|
| First-order reaction | $R^2$ | 0.932 | 0.851 | 0.925 | 0.903 | 0.894 | 0.881 |
| (data points = 12) | F | 137.28 | 56.93 | 122.88 | 93.46 | 83.95 | 427.48 |
| | p | <0.001 | <0.001 | <0.001 | <0.001 | <0.001 | <0.001 |
| Second-order reaction | $R^2$ | 0.97 | 0.903 | 0.938 | 0.935 | 0.913 | 0.913 |
| (data points = 12) | F | 324.74 | 93.56 | 151.11 | 143.96 | 113.08 | 607.03 |
| | p | <0.001 | <0.000 | <0.001 | <0.001 | <0.001 | <0.001 |
| Third-order reaction | $R^2$ | 0.992 | 0.921 | 0.932 | 0.937 | 0.911 | 0.914 |
| (data points = 12) | F | 1187.74 | 115.65 | 137.27 | 149.68 | 102.09 | 619.77 |
| | p | <0.001 | <0.000 | <0.001 | <0.001 | <0.001 | <0.001 |

Figure 16:
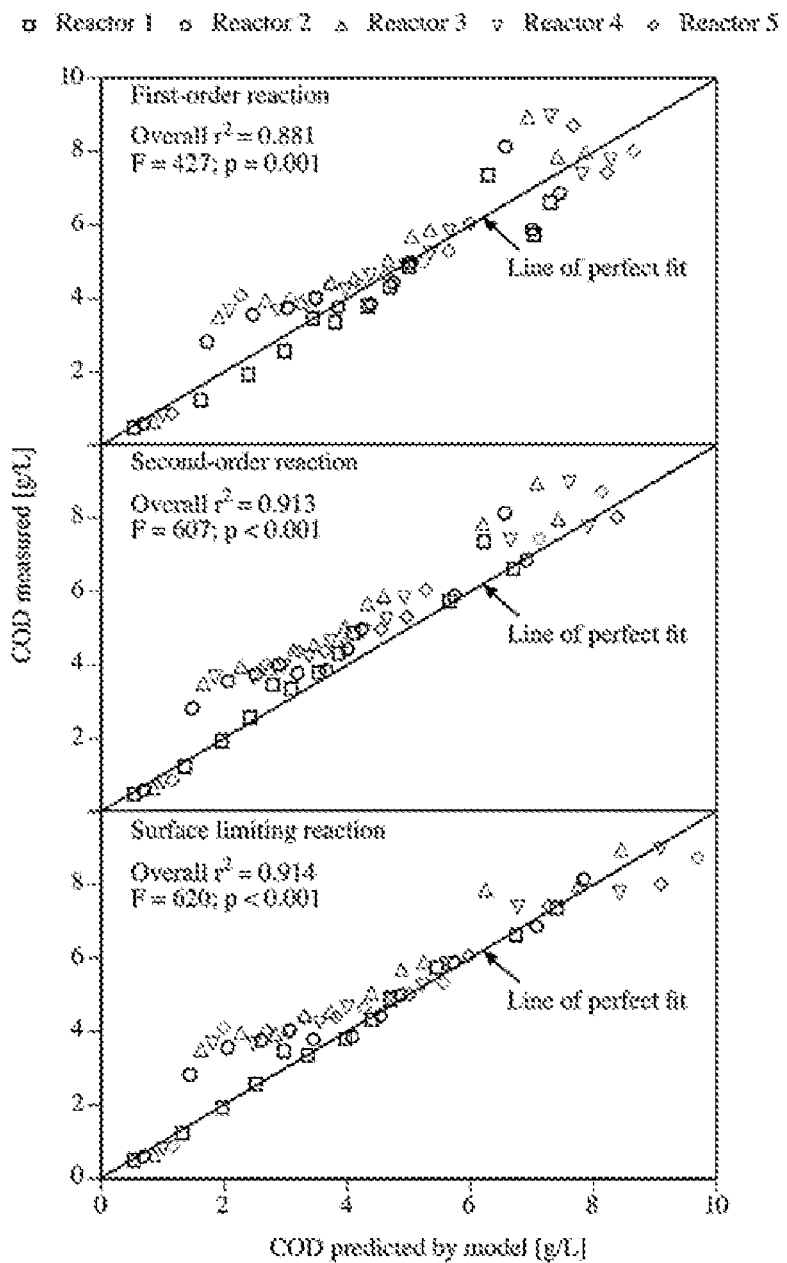
FIG. 16 is an illustration of overall comparisons of measured COD and predicted COD of three hydrolysis models.

The COD profiles predicted using the three hydrolysis reaction models were compared against the measured COD data for Reactors 1 to 5 in FIGS. 11 to 15. Overall, the surface-limiting reaction and the second-order reaction models fitted the measured data better than the first-order reaction model as shown by the line of perfect fit in FIG. 16. The trend and the closeness of fit of both the first-order and second-order reaction models deteriorated with time, while the trend and the fit of the surface-limiting reaction model was consistent throughout the full range of the tests. The substrate-to-microorganism ratio, $P_i/X$, was a limiting factor in the hydrolysis of particulate substrates, rather than the remaining substrate concentration $P_i$ as modeled by the first-order reaction model.

As $P_i$ decreased with time, soluble COD and X increased with time, and the ratio $P_i/X$ decreased. By incorporating this limitation, the surface limiting model predicted the COD better than the other two models. This is further corroborated by the fact that the COD generation did not increase in proportion to the enhancer dose.

The three hydrolysis models predicted COD generation reasonably well. The single-parameter, second-order model was more realistic than the first-order reaction model and easy to apply. The surface-limiting reaction model fitted the data with a slightly better quality of fit over the range tested and involved two parameters established experimentally.

EXAMPLE 5

Studies on anaerobic hydrolysis/acidogenesis of cattle manure to formulate, calibrate, and validate a new mechanistic model for the two processes were conducted. Native organisms in cattle manure residues were adequate to hydrolyze the particulate organics and to convert the solublized organics into fatty acids. The pH in all reactors remained below 5.5 under multiple combinations of manure-to-liquid ratios, and $CH_4$ content of the gas phase was less than 1%. Two additional similar reactors were run with a biocide and confirmed that the COD and volatile fatty acid (VFA) productions were due to the microbially mediated hydrolysis and acidogenesis. Advective and diffusive transport of the dissolved components was incorporated for application to down-flow lead-bed reactors. Experimental results from two leach-bed reactors fed with cattle manure residues at different bed porosities and recycle rates were gathered.

EXAMPLE 6

Membrane processes are implemented for hydrogen fuel cell and hydrogen separation. Binary Ru—Ni thin films are synthesized to act as novel fuel cell catalysts for hydrogen oxidation. A flash pyrolysis process is developed to deposit Ru—Ni nanoparticles with a core-and-shell structure. Hydrogen oxidation and permeation properties are investigated. The Ru—Ni nanoparticles are deposited on the surface of a sol-gel derived mesoporous γ-$Al_2O_3$ layer as the hydrogen selective separation membrane. The inorganic membranes have sufficiently large separation factors for hydrogen and significantly high resistances for membrane fouling.

Figure 17:
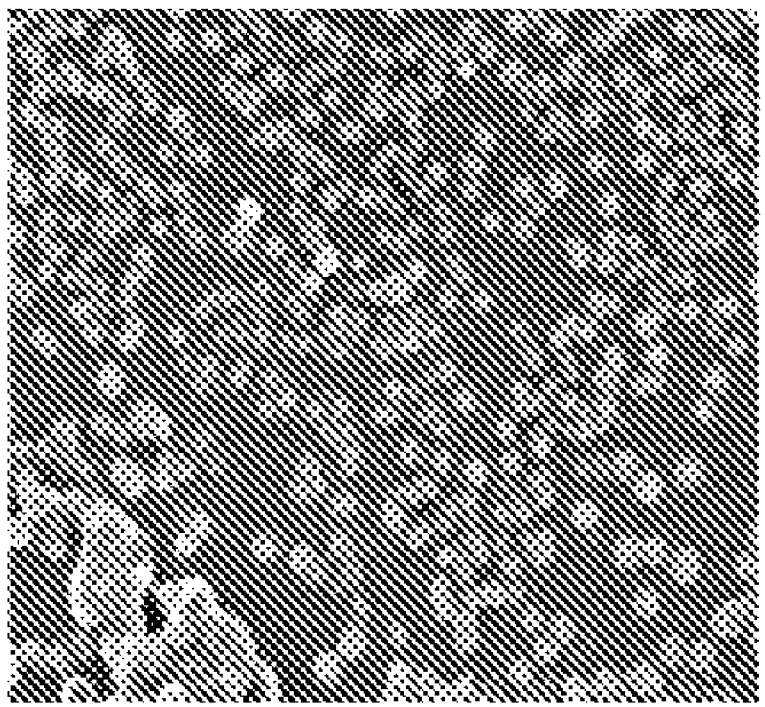
FIG. 17 is an illustration of a scanning electron microscope (SEM) image of binary Ru—Ni nanoparticles.
Figure 18:
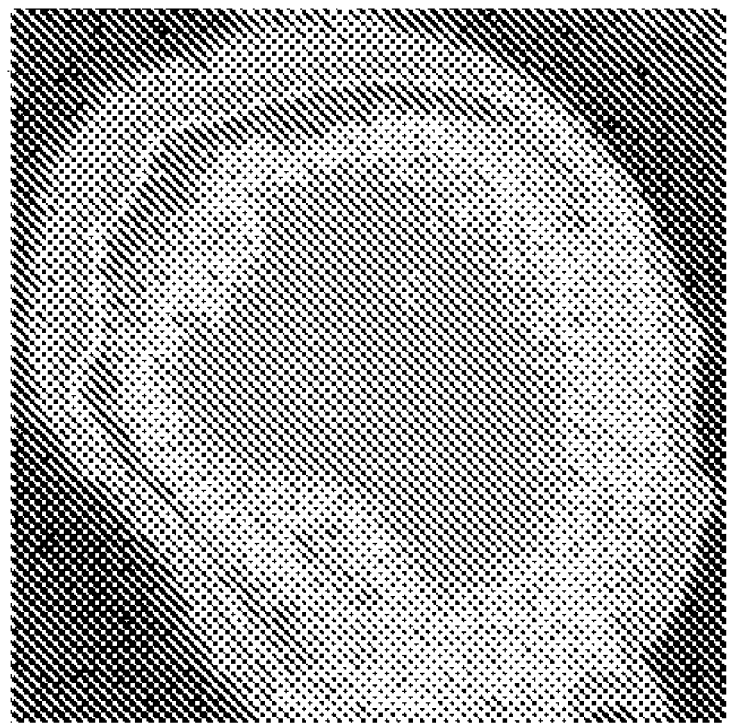
FIG. 18 is an illustration of an overall X-Ray mapping of nanoparticles with a core-and-shell structure of the Ru—Ni nanoparticles.

Binary Ru—Ni thin films are synthesized as novel fuel cell catalysts for hydrogen oxidation and for membrane processes for hydrogen fuel cell and hydrogen separation. Ru—Ni nanoparticles with core-and-shell structure were deposited by a flash pyrolysis process. A SEM image of the binary Ru—Ni nanoparticles is shown in FIG. 17, and the X-Ray mapping of a single Ru—Ni nanoparticle is shown in FIG. 18.

EXAMPLE 7

Key microbial groups are tracked by monitoring their populations as well as their metabolism. Microbial populations are tracked by combining culture-based detection methods with molecular-based detection. Populations which are metabolically useful (e.g. spore-formers potentially involved in hydrogen production) as well as pathogens harbored in the feedstock manure (e.g. fecal coliforms and subsets of fecal coliforms such as *E. coli* 0157) are monitored. A polymerase chain reaction (PCR) is employed to detect pathogenic bacteria, and PCR is used to track other groups of interest. To track the spore-formers in the sample (many of which produce hydrogen anaerobically), a spore cortex lytic enzyme gene is utilized, which is conserved among many *Clostridium* and *Bacillus* species using PCR primers. The culture-based assay for spore-formers involves pasteurization of the sample, then plating on non-selective medium grown under anaerobic conditions. Organisms that harbor the hydrogenase enzyme are monitored. For example, the hydrogenase gene in one of the sulfate-reducing bacteria produces hydrogen, and is sequenced; PCR primers track this common Ni—Fe type of hydrogenase. Indicator pathogens are enumerated using the membrane fecal coliform standard method, and representative pathogens such as *E. coli* are PCR-amplified utilizing primers specific for the attaching and effacing locus (eaeA) gene. Genetic characterization and manipulation is performed. Bacteria which play key roles in the bioconversion process and genetically characterize appropriate genes by, for example, sequencing PCR products of hydrogenase as well those involved in butyrate production are isolated. Genetically manipulating appropriate isolates in order to knock out genes that divert electron flow to products such as butyrate instead of hydrogen is accomplished. Site-directed mutagenesis is used. Gene knock-out mutants are tested in bioreactor studies to document changes in $H_2$ production efficiency.

EXAMPLE 8

Performance is characterized and tested. The reactor is operated at 30° C. in an environmental chamber. The photofermentation occurs under illumination of a 200 W/m² tungsten lamp. A pH controller is used to maintain the optimal pH for the two stages. Liquid samples collected from the two stages are analyzed for volatile acids, using gas chromatograph with FID; for optical density, using a spectrophotometer; and for COD, following standard methods. The gas production rate from each stage is measured using water columns. Gas samples are analyzed by gas chromatograph fitted with thermal conductivity detector. The operating parameter is the recirculation rate. Experiments are conducted under steady and cyclic illumination.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above and/or in the attachments, and of the corresponding application(s), are hereby incorporated by reference.

What is claimed is:

1. A method for producing gas from a biomaterial comprising the steps of:
   fermenting the biomaterial using anaerobic hydrolysis-fermentation;
   photofermentating;
   removing the gas;
   maintaining a pH during at least one stage of the method;
   the anaerobic hydrolysis-fermentation and the photofermentating take place in a single vessel comprising a multi-stage reactor and a gas-specific membrane;
   the multi-stage reactor comprising at least one leach-bed reactor and at least one suspended-growth reactor, the suspended-growth reactor in fluid communication with the leach-bed reactor; and
   the single vessel comprising a plurality of tubes, wherein a portion of the tubes divide the leach-bed reactor from the suspended-growth reactor within the single vessel, and an annular space between the tubes dividing the leach-bed reactor from the suspended-growth reactor.

2. The method of claim 1 wherein the anaerobic hydrolysis-fermentation and photofermentating occur in series.

3. The method of claim 1 wherein the anaerobic hydrolysis-fermentation comprises percolating leachate in a cross-flow mode.

4. The method of claim 1 wherein the anaerobic hydrolysis-fermentation comprises anaerobically fermenting leachate to produce a mixture comprising hydrogen gas, carbon dioxide, and fatty acids.

5. The method of claim 1 wherein the photofermentating comprises converting fatty acids to produce a mixture comprising hydrogen, carbon dioxide, and organic residue.

6. The method of claim 1 wherein the anaerobic hydrolysis-fermentation and photofermentating occur at room temperature.

7. The method of claim 1 wherein maintaining the pH comprises monitoring and controlling different pH levels in different stages.

8. The method of claim 1 further comprising maintaining hydrogen partial pressure and avoiding product inhibition.

9. The method of claim 1 wherein the anaerobic hydrolysis-fermentation occurs in a leach-bed reactor.

10. The method of claim 1 wherein the photofermentating occurs in a suspended-growth reactor stage.

11. The method of claim 1 wherein the biomaterial is a solid.

12. The method of claim 1 wherein the anaerobic hydrolysis-fermentation and photofermentating comprise utilizing naturally occurring organisms.

13. The method of claim 12 wherein the naturally occurring organisms occur in manure.

* * * * *